(12) United States Patent
Gruber et al.

(10) Patent No.: US 7,241,988 B2
(45) Date of Patent: Jul. 10, 2007

(54) SYSTEM AND METHOD OF SORTING MATERIALS USING HOLOGRAPHIC LASER STEERING

(75) Inventors: Lewis Gruber, Chicago, IL (US); Kenneth Bradley, Chicago, IL (US); Ward Lopes, Chicago, IL (US); Robert W. Lancelot, Chicago, IL (US); Joseph S. Plewa, Chicago, IL (US); David G. Grier, Chicago, IL (US)

(73) Assignee: Arryx, Inc., Chicago, IL (US)

( * ) Notice: Subject to any disclaimer, the term of this patent is extended or adjusted under 35 U.S.C. 154(b) by 110 days.

(21) Appl. No.: 10/630,904

(22) Filed: Jul. 31, 2003

(65) Prior Publication Data
US 2004/0089798 A1 May 13, 2004

Related U.S. Application Data

(60) Provisional application No. 60/399,386, filed on Jul. 31, 2002.

(51) Int. Cl.
G01N 21/63 (2006.01)

(52) U.S. Cl. .................. 250/251; 435/7.1; 435/288.7

(58) Field of Classification Search ............. 250/251, 250/484.4; 252/301.4 S, 301.4 H; 382/141, 382/143; 422/100
See application file for complete search history.

(56) References Cited

U.S. PATENT DOCUMENTS

| 3,649,829 | A |   | 3/1972  | Randolph         |
|-----------|---|---|---------|------------------|
| 3,960,449 | A |   | 6/1976  | Carleton et al.  |
| 4,325,706 | A |   | 4/1982  | Gershman et al.  |
| 4,409,106 | A |   | 10/1983 | Furuta et al.    |
| 4,424,132 | A |   | 1/1984  | Iriguchi         |
| 4,660,971 | A |   | 4/1987  | Sage et al.      |
| 4,667,830 | A |   | 5/1987  | Nozaki et al.    |
| 5,007,732 | A |   | 4/1991  | Ohki et al.      |
| 5,100,627 | A |   | 3/1992  | Buican et al.    |
| 5,180,065 | A |   | 1/1993  | Touge et al.     |
| 5,194,909 | A |   | 3/1993  | Tycko            |
| 5,229,297 | A |   | 7/1993  | Schnipelsky et al.|
| 5,483,469 | A |   | 1/1996  | Van den Engh et al.|
| 5,620,857 | A |   | 4/1997  | Weetall et al.   |
| 5,674,743 | A |   | 10/1997 | Ulmer            |
| 5,800,690 | A |   | 9/1998  | Chow et al.      |
| 5,837,115 | A |   | 11/1998 | Austin et al.    |
| 5,849,178 | A |   | 12/1998 | Holm et al.      |
| 5,879,625 | A |   | 3/1999  | Roslaniec et al. |
| 5,966,457 | A | * | 10/1999 | Lemelson ............ 382/141 |
| H001960   | H |   | 6/2001  | Conrad et al.    |

(Continued)

OTHER PUBLICATIONS

Paul O.P. Ts'o, "Basic Principles In Nucleic Acid Chemistry", National Library of Medicine, 1974, pp. 311-387, Academic Press, Inc., New York, New York.

*Primary Examiner*—Nikita Wells
*Assistant Examiner*—Johnnie L Smith, II
(74) *Attorney, Agent, or Firm*—Akerman Senterfitt; Jean C. Edwards, Esq.

(57) ABSTRACT

The present invention employs a beam steering apparatus to isolate valuable cells from other cells, tissues, and contaminants. In one embodiment, the system balances optical trapping against biasing flow to parallelize cell sorting under the flexible control of computer program-directed traps which differentially manipulate cells based on their composition or labels to direct separation.

71 Claims, 9 Drawing Sheets

U.S. PATENT DOCUMENTS

| | | |
|---|---|---|
| 6,368,871 B1 | 4/2002 | Christel et al. |
| 6,432,630 B1 | 8/2002 | Blankenstein |
| 6,451,264 B1 | 9/2002 | Bhullar et al. |
| 6,506,609 B1 | 1/2003 | Wada et al. |
| 6,524,860 B1 | 2/2003 | Seidel et al. |
| 6,637,463 B1 | 10/2003 | Lei et al. |
| 6,727,451 B1 | 4/2004 | Fuhr et al. |
| 6,815,664 B2 | 11/2004 | Wang et al. |
| 6,833,542 B2 | 12/2004 | Wang et al. |
| 6,838,056 B2 * | 1/2005 | Foster .................. 422/100 |
| 6,944,324 B2 * | 9/2005 | Tran et al. .................. 382/143 |
| 2002/0058332 A1 | 5/2002 | Quake et al. |
| 2002/0176069 A1 | 11/2002 | Hansen et al. |
| 2003/0032204 A1 * | 2/2003 | Walt et al. .................. 436/518 |
| 2003/0047676 A1 | 3/2003 | Grier et al. |
| 2003/0186426 A1 | 10/2003 | Brewer et al. |
| 2005/0061962 A1 * | 3/2005 | Mueth et al. .............. 250/251 |
| 2005/0121604 A1 * | 6/2005 | Mueth et al. .............. 250/251 |
| 2006/0152707 A1 | 7/2006 | Kanda |

* cited by examiner

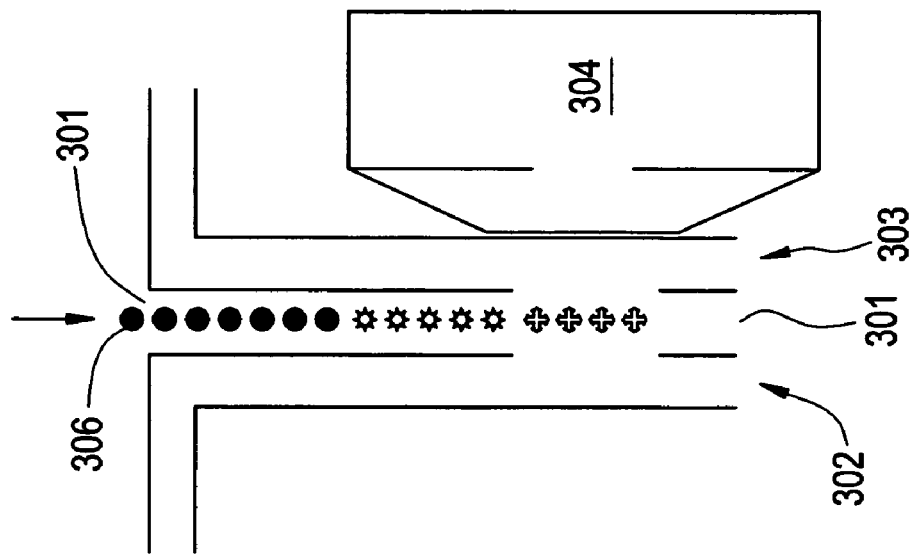
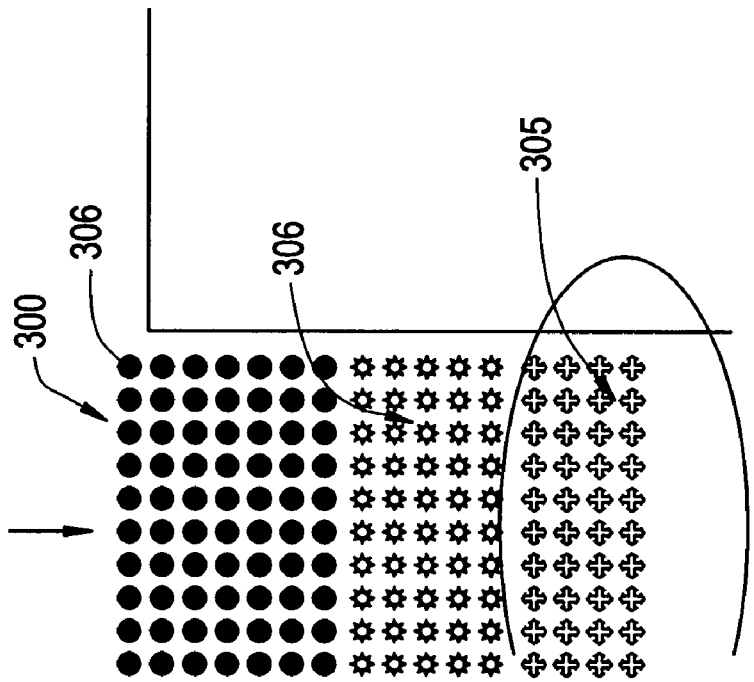

SYSTEM AND METHOD OF SORTING MATERIALS USING HOLOGRAPHIC LASER STEERING

The present invention claims priority from U.S. Provisional Patent Applications No. 60/399,386, filed Jul. 31, 2002, and No. 60/435,541, filed Dec. 20, 2002, the contents of which are herein incorporated by reference.

BACKGROUND OF THE INVENTION

The present invention relates to a system and method of sorting materials using laser steering, and in particular using holographic optical trapping.

In United States industry, there is a large number of unmet sorting and separation needs involving material made up of particles or units smaller than 50 microns. These needs range across industries from particle sizing and sample preparation in the specialty chemicals and materials fields including manufacturing products of nanotechnology, to protein selection and purification in the pharmaceutical and biotechnology industries. Other examples include cell sorting and selection, in the medical, diagnostic and agriculture sectors.

The importance of these needs can be seen by exploring the annual expenditures in areas where specialized or partial solutions have been developed, as well as by estimating the market value of sorted/separated/purified output in areas where there is currently not even a partial solution. As an example of the former, the biotechnology and pharmaceutical industries annually spend a huge amount on equipment and supplies for protein purification.

As an example of the latter, in the agricultural sector, there is currently no way to efficiently select the gender of offspring in farm animals; however, it is estimated that in the cattle area alone, value would be added by enabling such sperm selection as a part of the current artificial insemination process widely used in the industry.

Outside of the animal husbandry market, the purification process of islet cells from human pancreases is currently a large concern of medical scientists developing new treatment methods for Type I diabetes. Significant progress in islet transplantation methods has been made, but the purification problem is one of the remaining stumbling blocks. Traditional methods for purifying islet cells are inefficient and result in damage to the cells.

Islet cell transplantation is important because, in the Type I form of diabetes, the existing islet cells in the patient's pancreas have become damaged and no longer produce the insulin which is required for human survival. The current treatment for Type I diabetes involves injection of insulin 1 to 5 times per day. In spite of the treatment, the disease often leads to complications including blindness, blood flow problems requiring amputation, renal failure, and death. Greater purity and reduced contaminants for islet cells used in transplantation is expected to reduce the occurrence of these complications.

Of the approximately 1 million current sufferers of Type I diabetes in the United States, at least 50,000 sufferers per year would submit to islet cell transplantation if it were available. Upon large-scale acceptance of islet cell transplantation as an effective therapy, costs would be expected to jump substantially. The jump would be driven by the difficulty of using today's treatment method (frequent injections) and the severe consequences even when the current treatment is adequately administered.

Thus, islet purification is but one important problem requiring the highly selective sorting of human cells in a non-damaging, non-invasive way.

Another problem that needs to be addressed is the purification of normal cells from cancer cells in the bone marrow of persons undergoing whole-body radiation treatment for cancer.

Still another is the selection of stem cells for research into the causes of, and therapies for, diseases such as Parkinson's disease.

Yet another concern is developing new ways to automatically interrogate large numbers of human cells and select ones having characteristics not amenable to fluorescent tagging, which would enormously widen the scope and power of medical diagnoses.

One conventional technique in manipulating microscopic objects is optical trapping. An accepted description of the effect of optical trapping is that tightly focused light, such as light focused by a high numerical aperture microscope lens, has a steep intensity gradient. Optical traps use the gradient forces of a beam of light to trap a particle based on its dielectric constant. "Particle" refers to a biological or other chemical material including, but not limited to, oligonucleotides, polynucleotides, chemical compounds, proteins, lipids, polysaccharides, ligands, cells, antibodies, antigens, cellular organelles, lipids, blastomeres, aggregations of cells, microorganisms, peptides, cDNA, RNA and the like.

To minimize its energy, a particle having a dielectric constant higher than the surrounding medium will move to the region of an optical trap where the electric field is the highest. Particles with at least a slight dielectric constant differential with their surroundings are sensitive to this gradient and are either attracted to or repelled from the point of highest light intensity, that is, to or from the light beam's focal point. In constructing an optical trap, optical gradient forces from a single beam of light are employed to manipulate the position of a dielectric particle immersed in a fluid medium with a refractive index smaller than that of the particle, but reflecting, absorbing and low dielectric constant particles may also be manipulated.

The optical gradient force in an optical trap competes with radiation pressure which tends to displace the trapped particle along the beam axis. An optical trap may be placed anywhere within the focal volume of an objective lens by appropriately selecting the input beam's propagation direction and degree of collimation. A collimated beam entering the back aperture of an objective lens comes to a focus in the center of the lens' focal plane while another beam entering at an angle comes to a focus off-center. A slightly diverging beam focuses downstream of the focal plane while a converging beam focuses upstream. Multiple beams entering the input pupil of the lens simultaneously each form an optical trap in the focal volume at a location determined by its angle of incidence. The holographic optical trapping technique uses a phase modifying diffractive optical element to impose the phase pattern for multiple beams onto the wavefront of a single input beam, thereby transforming the single beam into multiple traps.

Phase modulation of an input beam is preferred for creating optical traps because trapping relies on the intensities of beams and not on their relative phases. Amplitude modulations may divert light away from traps and diminish their effectiveness.

When a particle is optically trapped, optical gradient forces exerted by the trap exceed other radiation pressures arising from scattering and absorption. For a Gaussian $TEM_{00}$ input laser beam, this generally means that the beam diameter should substantially coincide with the diameter of the entrance pupil. A preferred minimum numerical aperture to form a trap is about 0.9 to about 1.0.

One difficulty in implementing optical trapping technology is that each trap to be generated generally requires its own focused beam of light. Many systems of interest require multiple optical traps, and several methods have been developed to achieve multiple trap configurations. One existing method uses a single light beam that is redirected between multiple trap locations to "time-share" the beam between various traps. However, as the number of traps increases, the intervals during which each trap is in its "off" state may become long for particles to diffuse away from the trap location before the trap is re-energized. All these concerns have limited implementations of this method to less than about 10 traps per system.

Another traditional method of creating multi-trap systems relies on simultaneously passing multiple beams of light through a single high numerical aperture lens. This is done by either using multiple lasers or by using one or more beam splitters in the beam of a single laser. One problem with this technique is that, as the number of traps increases, the optical system becomes progressively more and more complex. Because of these problems, the known implementations of this method are limited to less than about 5 traps per system.

In a third approach for achieving a multi-trap system, a diffractive optical element (DOE) (e.g., a phase shifting hologram utilizing either a transmission or a reflection geometry) is used to alter a single laser beam's wavefront. This invention is disclosed in U.S. Pat. No. 6,055,106 to Grier et al. The wavefront is altered so that the downstream laser beam essentially becomes a large number of individual laser beams with relative positions and directions of travel fixed by the exact nature of the diffractive optical element. In effect, the Fourier transform of the DOE produces a set of intensity peaks each of which act as an individual trap or "tweezer."

Some implementations of the third approach have used a fixed transmission hologram to create between 16 and 400 individual trapping centers.

A fixed hologram has been used to demonstrate the principle of holographic optical trapping but using a liquid crystal grating as the hologram permitted 'manufacture' of a separate hologram for each new distribution of traps. The spatially varying phase modulation imposed on the trapping laser by the liquid crystal grating may be easily controlled in real time by a computer, thus permitting a variety of dynamic manipulations.

Other types of traps that may be used to optically trap particles include, but are not limited to, optical vortices, optical bottles, optical rotators and light cages. An optical vortex produces a gradient surrounding an area of zero electric field which is useful to manipulate particles with dielectric constants lower than the surrounding medium or which are reflective, or other types of particles which are repelled by an optical trap. To minimize its energy, such a particle will move to the region where the electric field is the lowest, namely the zero electric field area at the focal point of an appropriately shaped laser beam. The optical vortex provides an area of zero electric field much like the hole in a doughnut (toroid). The optical gradient is radial with the highest electric field at the circumference of the doughnut. The optical vortex detains a small particle within the hole of the doughnut. The detention is accomplished by slipping the vortex over the small particle along the line of zero electric field.

The optical bottle differs from an optical vortex in that it has a zero electric field only at the focus and a non-zero electric field in all other directions surrounding the focus, at an end of the vortex. An optical bottle may be useful in trapping atoms and nanoclusters which may be too small or too absorptive to trap with an optical vortex or optical tweezers. (See J. Arlt and M. J. Padgett. "Generation of a beam with a dark focus surrounded by regions of higher intensity: The optical bottle beam," Opt. Lett. 25, 191–193, 2000.)

The light cage (U.S. Pat. No. 5,939,716) is loosely, a macroscopic cousin of the optical vortex. A light cage forms a time-averaged ring of optical traps to surround a particle too large or reflective to be trapped with dielectric constants lower than the surrounding medium.

When the laser beam is directed through or reflected from the phase patterning optical element, the phase patterning optical element produces a plurality of beamlets having an altered phase profile. Depending on the number and type of optical traps desired, the alteration may include diffraction, wavefront shaping, phase shifting, steering, diverging and converging. Based upon the phase profile chosen, the phase patterning optical element may be used to generate optical traps in the form of optical traps, optical vortices, optical bottles, optical rotators, light cages, and combinations of two or more of these forms.

With respect to the manipulation of materials, tweezing of viruses and bacteria has been demonstrated in addition to tweezing of dielectric spheres. In addition to prokaryotes and viruses, a large variety of protists such as *Tetrahymena thermophila* has been successfully tweezed. Furthermore, both somatic cells such as eukocytes and epithelial cheek cells, and germ line cells such as spermatozoa have been trapped and manipulated.

Researchers have sought indirect methods for manipulating cells, such as tagging the cells with diamond microparticles and then tweezing the diamond particles. Cell manipulations have included cell orientation for microscopic analysis as well as stretching cells. Tissue cells have also been arranged with tweezers in vitro in the same spatial distribution as in vivo.

In addition to the cells themselves, optical tweezers have been used to manipulate cellular organelles, such as vesicles transported along microtubules, chromosomes, or globular DNA. Objects have also been inserted into cells using optical tweezers.

A variety of sorting processes for biological purposes is also possible with optical tweezers. Cell sorting using traditional optical trapping for assays and chromosome collection and sorting to create libraries have already been demonstrated. Cell assays for drug screening have also been developed.

Accordingly, as an example of new types of sorting using laser steered optical traps, a method of cell sorting using a technique which isolates valuable cells from other cells, tissues, and contaminants is needed. Further, a way of achieving a unique contribution of optical trapping to the major industrial needs of (cell) sorting and purification is required. Still further, there is a need to separate sperm cells in the animal husbandry market.

SUMMARY OF THE INVENTION

The present invention relates to a system and method of sorting materials using laser steering, and in particular using holographic optical trapping.

In one embodiment consistent with the present invention, optical trapping, which is a technology which has been used as a tool for manipulating microscopic objects, is used. An accepted description of the effect is that tightly focused light, such as light focused by a high numerical aperture microscope lens, has a steep intensity gradient. Optical traps use the gradient forces of a beam of light to trap a particles based on its dielectric constant To minimize its energy, a particle having a dielectric constant higher than the surrounding medium will move to the region of an optical trap where the electric field is the highest.

Optical trapping of the present invention is used to address cell sorting and purification in several ways. For example, the forces exerted by optical traps on a material are sensitive to the exact distribution of the dielectric constant in that material—the optical force therefore depends on the composition and shape of the object.

Further, other forces on the object are sensitive to the hydrodynamic interaction between the object and the surrounding fluid—control of the fluid flow probes material shape, size and such features as surface rugosity.

Still further, localizing an object at a known position allows additional methods of automated interrogation such as high speed imaging and particle-specific scattering measurements.

In one embodiment consistent with the present invention, in achieving a multi-trap system, a diffractive optical element (DOE, i.e., a phase shifting hologram utilizing either a transmission or a reflection geometry) is used to alter a single laser beam's wavefront. The wavefront is altered so that the downstream laser beam essentially becomes a large number of individual laser beams with relative positions and directions of travel fixed by the exact nature of the diffractive optical element.

The present invention provides optical trapping by focusing a laser beam with a lens to create an optical trap wherein the lens has a numerical aperture less than 0.9, and preferably decreases until it is most preferably less than 0.1.

Sorting using holographic laser steering involves establishing classes of identification for objects to be sorted, introducing an object to be sorted into a sorting area, and manipulating the object with a steered laser according to its identity class. The manipulation may be holding, moving, rotating, tagging or damaging the object in a way which differs based upon its identity class. Thus, the present invention provides a way of implementing a parallel approach to cell sorting using holographic optical trapping.

In one embodiment of the present invention, spectroscopy of a sample of biological material may be accomplished with an imaging illumination source suitable for either inelastic spectroscopy or polarized light back scattering, the former being useful for assessing chemical identity, and the latter being suited for measuring dimensions of internal structures such as the nucleus size. Using such spectroscopic methods, in some embodiments, cells are interrogated. The spectrum of those cells which had positive results (i.e., those cells which reacted with or bonded with a label) may be obtained by using this imaging illumination.

A computer program may analyze the spectral data to identify the desired targets (i.e., cells bearing either an X or Y chromosome, or a suspected cancerous, pre-cancerous and/or non-cancerous cell types, etc.), then may apply the information to direct the phase patterning optical element (i.e., optical traps) to segregate or contain those desired or selected targets (i.e., cell types). The contained cells may be identified based on the reaction or binding of the contained cells with chemicals, or by using the natural fluorescence of the object, or the fluorescence of a substance associated with the object, as an identity tag or background tag. Upon completion of the assay, selection may be made, via computer and/or operator, of which cells to discard and which to collect.

Manipulation of cells in general, is made safer by having multiple beams available. Like a bed of nails, multiple tweezers ensure that less power is introduced at any particular spot in the cell. This eliminates hot spots and reduces the risk of damage. Any destructive two-photon processes benefit greatly since the absorption is proportional to the square of the laser power. Just adding a second tweezer decreases two-photon absorption in a particular spot by a factor of four. Large cells like *Tetrahymena* involves a large amount of laser power for effective trapping. Putting the power into a single trap may cause immediate damage to the cell.

The manipulation of even just a single cell is greatly enhanced by utilizing holographic optical trapping, for example. A single epithelial cheek cell may be manipulated by a line of tweezers, which lift the cell along the perimeter on one side. The resulting rotation allows a 360 degree view of the cell. In addition to the advantage for viewing of biological samples, there also exists the ability to orient samples stably, which has clear benefit for studies such as scattering experiments which have a strong dependence on orientation of the sample.

Sorting with a wide field of view has many advantages such as higher throughput. However, standard tweezing in a WFOV may fails du to excessive radiation pressure. Tweezing with a wide field of view using holographic optical trapping may permit the ability to form exotic modes of light which greatly reduce the radiation pressure of the light beam. Vortex traps, for example, have a dark center because the varying phases of light cancel in the center of the trap. This dark center means most of the rays of light which travel down the center of the beam no longer exist. It is exactly these beams which harbor most of the radiation pressure of the light, so their removal greatly mitigates the difficulty in axial trapping. Other modes, e.g., donut modes, have the same advantage.

In one embodiment consistent with the present invention, the method and system lends itself to a semi-automated or automated process for tracking the movement and contents of each optical trap. In one embodiment consistent with the present invention, movement may be monitored via an optical data stream which can be viewed, or converted to a video signal, monitored, or analyzed by visual inspection of an operator, spectroscopically, and/or by video monitoring. The optical data stream may also be processed by a photodetector to monitor intensity, or any suitable device to convert the optical data stream to a digital data stream adapted for use by a computer and program. The computer program controls the selection of cells and the generation of optical traps.

In other embodiments consistent with the present invention, the movement of cells is tracked based on predetermined movement of each optical trap caused by encoding the phase patterning optical element. Additionally, in some embodiments, a computer program maintains a record of each cell contained in each optical trap.

In one embodiment consistent with the present invention, cell sorting of X and Y sperm for animal husbandry is performed.

In the beef cattle industry, the ability to change the male/female ratio of the offspring from the current 50%:50% mix to an 85%:15% mix would dramatically increase the value of the annual offspring. A similar, though smaller, increase in value would occur in the dairy industry.

In one embodiment consistent with the present invention, a method of sorting objects includes the steps of introducing the objects into an input channel at a predetermined flow rate; funneling the objects using a beam steering apparatus; evaluating the objects to determine which meet a predetermined criteria; and sorting the objects which meet said criteria from objects which do not meet said criteria.

In another embodiment consistent with the present invention, a method of sorting objects includes the steps of distributing the objects over a surface of a structure; and evaluating the objects in said structure according to a predetermined criteria using a beam steering apparatus.

In yet another embodiment consistent with the present invention, a method of sorting objects includes the steps of distributing the objects in a gel; detecting the objects which meet a predetermined criteria; and sorting the objects which meet said criteria from objects which do not meet said criteria.

In yet another embodiment consistent with the present invention, an apparatus for sorting objects includes a plurality of optical traps formed using an optical trapping apparatus; an input channel into which the objects are introduced at a predetermined flow rate; and at least one output channel; wherein the objects are sorted according to predetermined criteria using said optical traps in a sorting region prior to entering said output channel.

In yet another embodiment consistent with the present invention, an apparatus for sorting objects includes a beam steering apparatus; and a structure having a surface on which the objects are distributed; wherein the objects are sorted using said bean steering apparatus, according to whether the objects meet predetermined criteria.

In yet another embodiment consistent with the present invention, an apparatus for sorting objects includes means for introducing the objects into an input channel at a predetermined flow rate; means for funneling the objects; means for evaluating the objects to determine which objects meet predetermined criteria; and means for sorting the objects which meet said criteria from objects which do not meet said criteria.

In yet another embodiment consistent with the present invention, an apparatus for sorting objects includes means for distributing the objects over a surface of a structure; and means for evaluating the objects in said structure according to predetermined criteria using a beam steering apparatus.

In yet another embodiment consistent with the present invention, an apparatus for sorting objects includes means for distributing the objects in a gel; means for detecting the objects which meet a predetermined criteria; and means for sorting the objects which meet said criteria from objects which do not meet said criteria.

In yet another embodiment consistent with the present invention, a method of sorting objects includes the steps of accessing an object using an optical trap; examining said object to determine its identity; and sorting said identified object according to predetermined criteria.

In yet another embodiment consistent with the present invention, an apparatus for sorting objects includes means for accessing an object using an optical trap; means for examining said object to determine its identity; and means for sorting said identified object according to predetermined criteria.

In yet another embodiment consistent with the present invention, an apparatus for sorting objects includes a beam steering apparatus including: a laser which provides a laser beam for illumination; a diffractive optical element which diffracts said beam into a plurality of beamlets; and an objective lens which converges the beamlet, thereby producing optical gradient conditions resulting in an optical data stream to form an optical trap; and a sample chamber into which the objects are introduced, trapped and sorted.

In yet another embodiment consistent with the present invention, a method of manipulating objects includes introducing the objects into an evaluation system; evaluating the objects according to a predetermined criteria using a beam steering apparatus; and manipulating the objects according to said predetermined criteria using said beam steering apparatus.

In yet another embodiment consistent with the present invention, a method of destroying objects includes accessing an object using a beam steering apparatus; examining said object to determine its identity; sorting said identified object according to predetermined criteria; and destroying said identified object when said object meets said predetermined criteria.

Finally, in yet another embodiment consistent with the present invention, an apparatus for destroying objects includes means for accessing an object using a beam steering apparatus; means for examining said object to determine its identity; means for sorting said identified object according to predetermined criteria; and means for destroying said identified object when said object meets said predetermined criteria.

There has thus been outlined, rather broadly, some features consistent with the present invention in order that the detailed description thereof that follows may be better understood, and in order that the present contribution to the art may be better appreciated. There are, of course, additional features consistent with the present invention that will be described below and which will form the subject matter of the claims appended hereto.

In this respect, before explaining at least one embodiment consistent with the present invention in detail, it is to be understood that the invention is not limited in its application to the details of construction and to the arrangements of the components set forth in the following description or illustrated in the drawings. Methods and apparatuses consistent with the present invention are capable of other embodiments and of being practiced and carried out in various ways. Also, it is to be understood that the phraseology and terminology employed herein, as well as the abstract included below, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the methods and apparatuses consistent with the present invention.

BRIEF DESCRIPTION OF THE DRAWINGS

FIGS. 7A and 7B illustrate schematic front and side views, respectively, of the funneling traps according to one embodiment consistent with the present invention.

DETAILED DESCRIPTION OF THE INVENTION

Figure 1:
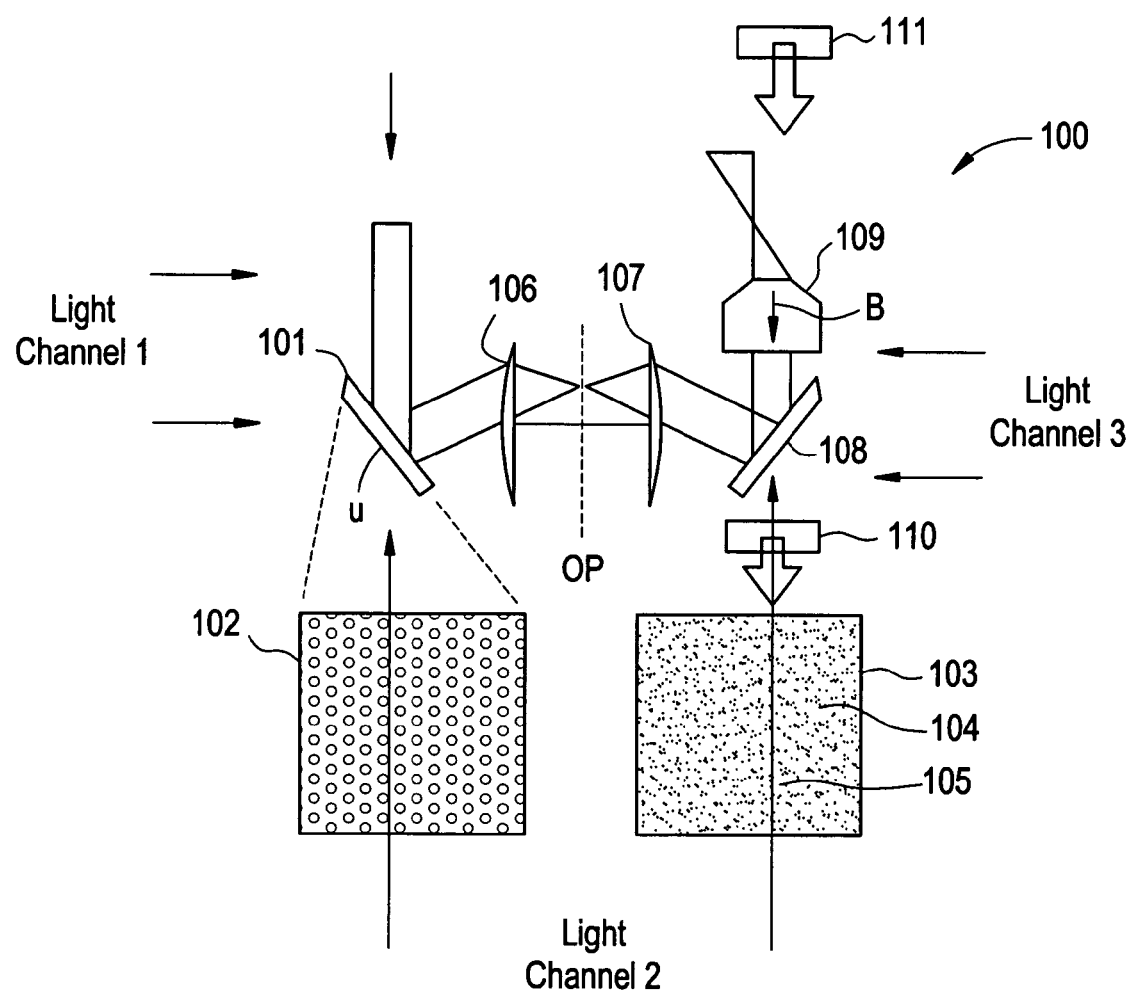
FIG. 1 schematically illustrates a holographic optical trapping system according to one embodiment consistent with the present invention.

In a holographic optical trapping apparatus or system 100 as illustrated in FIG. 1, light is incident from a laser system, and enters as shown by the downward arrow, to power the system 100.

A phase patterning optical element 101 is preferably a dynamic optical element (DOE), with a dynamic surface, which is also a phase-only spatial light modulator (SLM) such as the "PAL-SLM series X7665," manufactured by Hamamatsu of Japan, the "SLM 512SA7" or the "SLM 512SA15" both manufactured by Boulder Nonlinear Systems of Lafayette, Colo. These dynamic phase patterned optical elements 101 are computer-controlled to generate the beamlets by a hologram encoded in the medium which may be varied to generate the beamlets and select the form of the beamlets. A phase pattern 1–2 generated on the lower left of FIG. 1 produces the traps 103 shown in the lower right filled with 1 μm diameter silica spheres 104 suspended in water 105. Thus, the system 100 is controlled by the dynamic hologram shown below on the left.

The laser beam travels through lenses 106, 107, to dichroic mirror 108. The beam splitter 108 is constructed of a dichroic mirror, a photonic band gap mirror, omni directional mirror, or other similar device. The beam splitter 108 selectively reflects the wavelength of light used to form the optical traps 103 and transmits other wavelengths. The portion of light reflected from the area of the beam splitter 108 is then passed through an area of an encoded phase patterning optical element disposed substantially in a plane conjugate to a planar back aperture of a focusing (objective) lens 109.

In single beam optical trapping (also called laser or optical tweezers) it had been thought, prior to the present invention, that a high numerical aperture lens was necessary for acceptable optical traps. A basis for this thinking was that, for optical trapping, one uses the gradient in the electric field of the impinging light to trap the particle. In order to have a large trapping force it has been thought necessary to have a large gradient in the electric field (or number density of rays). The way that one usually accomplishes this is to pass the light field through a high numerical aperture lens.

A concern with observation and trapping of samples within a large field of view is that such observation and trapping would involve an objective lens with a low numerical aperture. Contrary to prior teaching, the present invention provides a low numerical aperture lens as, for example, the objective lens 109 in FIG. 1. The ability to observe and trap in this situation could be useful in any application where one would benefit from a large field of view given by a low magnification lens, such as placing microscopic manufactured parts or working with large numbers of objects, such as cells, for example.

As an example according to the present invention, 3 micron silica spheres 104 suspended in water 105 were trapped with lenses 109 with an unprecedented low numerical aperture. The lenses 109 used were manufactured by Nikon:

(a) Plan 4× with an NA of 0.10; and
(b) Plan 10× with an NA of 0.25.

Suitable phase patterning optical elements are characterized as transmissive or reflective depending on how they direct the focused beam of light or other source of energy. Transmissive diffractive optical elements transmit the beam of light or other source of energy, while reflective diffractive optical elements reflect the beam.

The phase patterning optical element 101 may also be categorized as having a static or a dynamic surface. Examples of suitable static phase patterning optical elements include those with one or more fixed surface regions, such as gratings, including diffraction gratings, reflective gratings, and transmissive gratings, holograms, including polychromatic holograms, stencils, light shaping holographic filters, polychromatic holograms, lenses, mirrors, prisms, waveplates and the like. The static, transmissive phase patterning optical element is characterized by a fixed surface.

However, in some embodiments, the phase patterning optical element 101 itself is movable, thereby allowing for the selection of one more of the fixed surface regions by moving the phase patterning optical element 101 relative to the laser beam to select the appropriate region.

The static phase patterning optical element may be attached to a spindle and rotated with a controlled electric motor (not shown). The static phase patterning optical element has a fixed surface and discrete regions. In other embodiments of static phase patterning optical elements, either transmissive or reflective, the fixed surface has a non-homogeneous surface containing substantially continuously varying regions, or a combination of discrete regions, and substantially continuously varying regions.

Examples of suitable dynamic phase patterning optical elements having a time dependent aspect to their function include computer-generated diffractive patterns, phase-shifting materials, liquid crystal phase-shifting arrays, micromirror arrays, including piston mode micro-mirror arrays, spatial light modulators, electro-optic deflectors, accousto-optic modulators, deformable mirrors, reflective MEMS arrays and the like. With a dynamic phase patterning optical element 101, the medium 105 which comprises the phase patterning optical element 101 encodes a hologram which may be altered, to impart a patterned phase shift to the focused beam of light which results in a corresponding change in the phase profile of the focused beam of light, such as diffraction, or convergence. Additionally, the medium 105 may be altered to produce a change in the location of the optical traps 103. It is an advantage of dynamic phase patterning optical elements 101, that the medium 105 may be altered to independently move each optical trap 103.

In those embodiments in which the phase profile of the beamlets is less intense at the periphery and more intense at regions inward from the periphery, overfilling the back aperture by less than about 15 percent is useful to form optical traps with greater intensity at the periphery, than optical traps formed without overfilling the back aperture.

In some embodiments, the form of an optical trap may be changed from its original form to that of a point optical trap, an optical vortex, Bessel beam, an optical bottle, an optical rotator or a light cage The optical trap may be moved in two or three dimensions. The phase patterning optical element is also useful to impart a particular topological mode to the laser light, for example, by converting a Gaussian into a Gauss-Laguerre mode. Accordingly, one beamlet may be formed into a Gauss-Laguerre mode while another beamlet may be formed in a Gaussian mode. The utilization of Gauss-Laguerre modes greatly enhances trapping by reducing radiation pressure.

1. Imaging System

Figure 5:
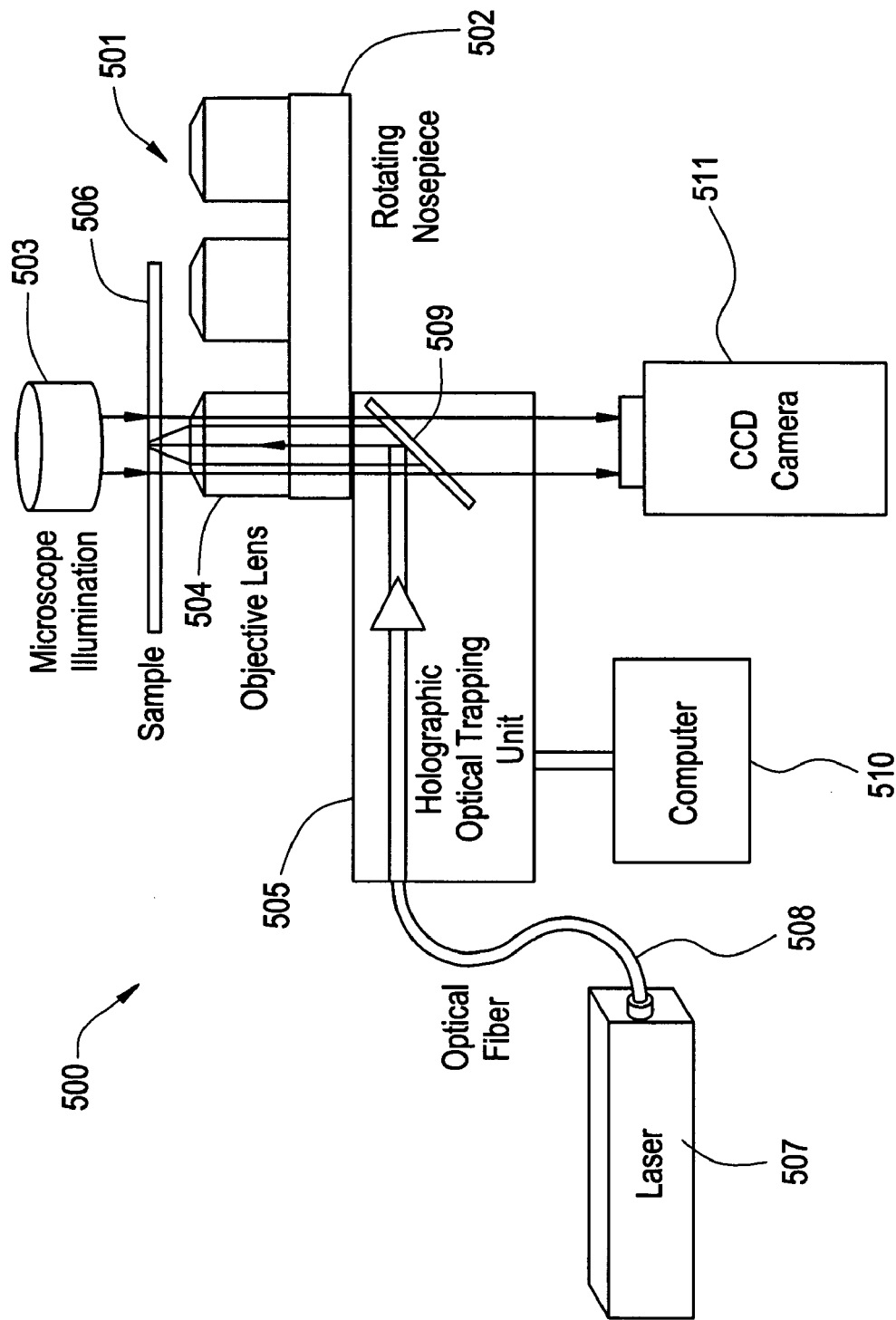
FIG. 5 is a schematic diagram of a holographic optical trapping system for sorting objects according to one embodiment consistent with the present invention.

The current instrument design uses a high resolution CCD camera for the primary imaging system 110. The main advantage of the CCD camera (see reference numeral 511 in FIG. 5) is the favorable cost/performance ratio since this technology is a mature one. Another advantage of CCD cameras is their wide dynamic range and the ease of generating digital output.

The images are viewed on a computer screen (see reference numeral 510 in FIG. 5) to provide both a frame of reference for selecting the location of the traps as well as to minimize the possibility of inadvertent exposure of the operator to the laser.

2. User Interface a. Object Display

The user interface consists of a computer screen which displays the field of view acquired by the CCD camera. The user designates the loci of the traps with a mouse. There is also an option to delete a location.

As described in greater detail below, the user is also able to specify the power per trap so as to be able to avoid specimen damage. In addition it is desirable to be able to vary trap power because trapping depends upon the difference between the index of refraction of the specimen and the suspending medium which can be expected to vary from specimen to specimen.

b. The Hologram

The purpose of designating the loci of the traps is to provide input for the hologram calculation. The hologram is essentially a function whose Fourier transform produces the desired trap array. However in the case of the liquid crystal display this function is a phase object (i.e., an object that changes the phase of the wavefront without absorbing any energy c. Methods for Choosing the Set of Traps When a large number of traps are needed, the time to designate their location with a computer mouse may be inordinately long. Therefore, there are several options to reduce the time required.

Often one wishes to use the traps to move an object in a particular direction. This may be accomplished by using the mouse to create a line (by dragging). The computer program interprets a line as calling for a series of traps to be deployed sequentially and sufficiently close together so as to move the target in small steps without losing the lock on the target.

The present invention also includes the capability of changing the height of the traps. If a laser beam is parallel to the optical axis of the objective lens 109, then a trap forms at the same height as the focal plane of the lens 109. Changing the height of a trap is accomplished by adjusting the hologram so that the beam of light forming a trap is slightly converging (or diverging) as it enters the objective lens 109 of the microscope. Adjusting the height of a trap is possible using lenses but only a holographic optical trapping (HOT) allows the height of each individual trap to be adjusted independently of any other trap. This is accomplished by the computer program adjusting the phase modulation caused by the liquid crystal hologram.

3. Sample Holder a. General

Figure 2A:
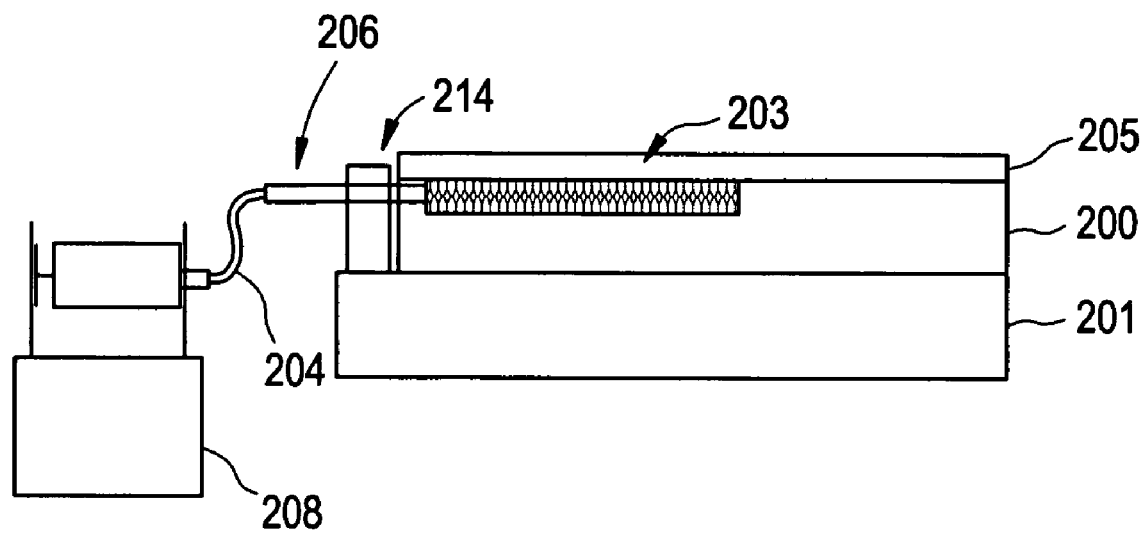
FIGS. 2A and 2B are a side view schematic diagram and a top view schematic diagram, respectively, showing a sample being introduced into sample holder, according to one embodiment consistent with the present invention.

The sample chamber 200 (see FIGS. 2A and 2B) of the present invention is inexpensive and disposable. Although the sample chamber 200 of the present invention is described below, another object of the present invention is to create a flexible design that may be changed for differing applications.

The sample chamber 200 lies on the surface of a microscope slide 201. The sample chamber 200 contains a series of channels 203 for introducing specimens or objects. The channels 203 are connected to supply and collection reservoirs by thin tubing 204 (commercially available). Samples or objects will be suspended in a liquid medium and will be introduced into the working area via the channels 203. The sample chamber 200 is covered by a cover slip 205.

b. Manufacture of the Sample Chamber

In one embodiment consistent with the present invention, a poly(dimethyl siloxane) (PDMS) resin is used to fabricate the chamber 200. The process involves creating the desired pattern of channels 203 on a computer using standard CAD/CAM methods and transferring the pattern to a photomask using conventional photoresist/etching techniques. The photomask is then used as a negative mask to create an inverse pattern of channels which are etched on a silicon wafer. The depth of the channels 203 is controlled by the etch time. The silicon wafer is a negative replica of the actual sample chamber 200. The final step consists of creating the positive sample chamber 200 by pouring PDMS onto the wafer and polymerizing. This results in a PDMS mold which is bonded to a glass slide 201 and overlaid with a cover slip 205. The glass to PDMA bonding is effected with an oxygen etch which activates the exposed surfaces.

A number of additional steps are necessary to ensure consistent quality. For instance the PDMS solution/hardner is maintained under a vacuum in order to prevent bubble formation. The silicon wafer is silanized to prevent the PDMS from sticking to the wafer. There are a variety of steps involving cleaning the replicas and maintaining proper environmental controls. These represent standard technology.

The channels 203 are connected to microbore tubing 204 using small syringe needles 206 held using glue 214, which are inserted through the PDMS mold into small circular wells 207 which connect to each channel 203. Sample solutions are introduced into the channel 203 using micropumps 208.

Figure 2B:
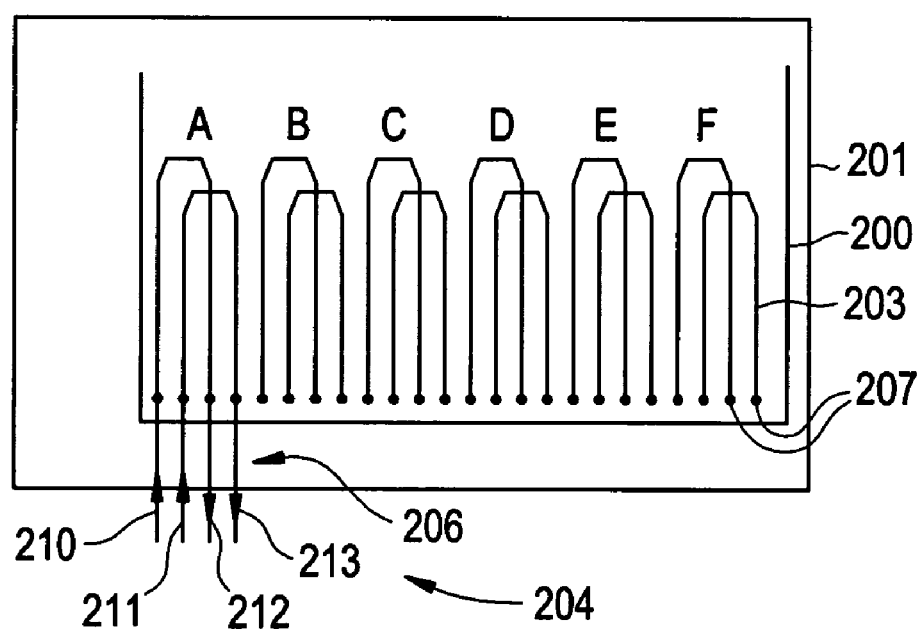

FIG. 2B shows a diagram of a typical arrangement for the introduction of a sample via the syringe pump 208 at 210. The medium is introduced at 211, and waste is collected at 21 and the desired collections at 213.

Figure 3:
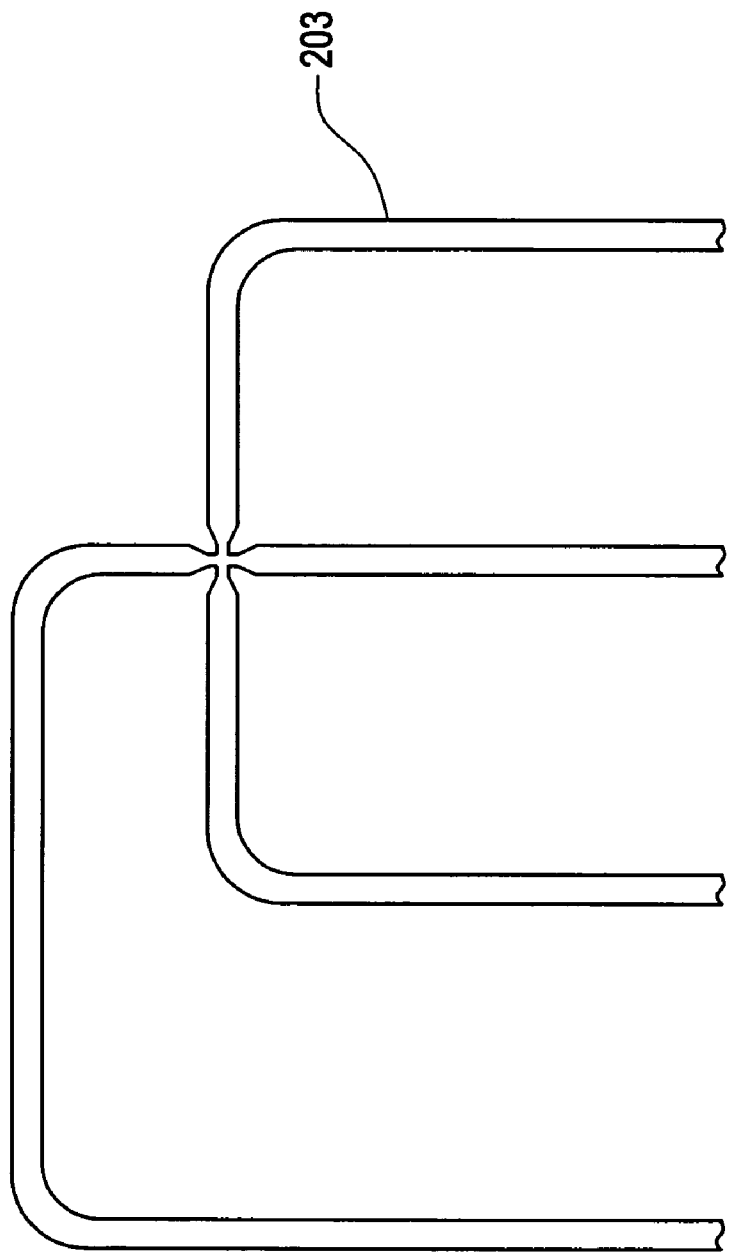
FIG. 3 depicts a scanning electron micrograph of a sample chamber according to one embodiment consistent with the present invention.
Figure 4:
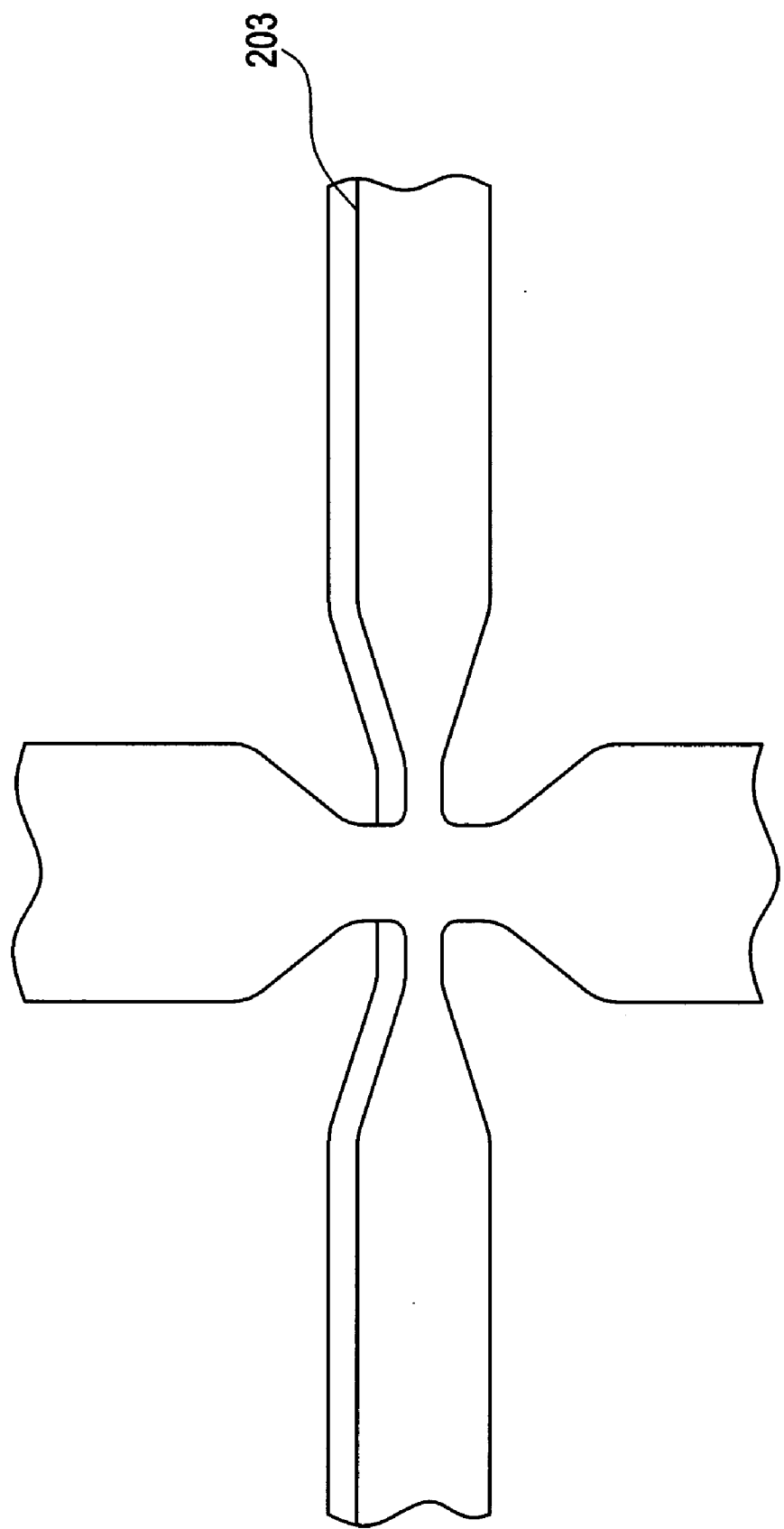
FIG. 4 shows an enlarged view of the working area of a sample chamber according to one embodiment consistent with the present invention.

FIG. 3 presents a representation of a scanning electron micrograph of the diagram in FIG. 2B as actually created from the process described above. The channels are approximately 50 microns wide and 50 microns deep. FIG. 4 presents a representation of a scanning electron micrograph of the 'working' volume where manipulations of the specimen under study would occur. The diagrams clearly show that the channels 203 are smooth and clean. Although the channels 203 are rectangular in cross-section, other shapes may be devised as well. The channels 203 are designed to allow samples to be flowed to a 'working area' whose shape may be custom designed for experimental requirements.

c. Holographic Optical Traps

Unlike scanned optical traps which address multiple trapping points in sequence, and thus are time-shared, holographic optical traps illuminate each of their traps continuously. For a scanned optical trap to achieve the same trapping force as a continuously illuminated trap, it must provide at least the same time-averaged intensity. This means that the scanned trap has to have a higher peak intensity by a factor proportional to at least the number of trapping regions. This higher peak intensity increases the opportunities for optically-induced damage in the trapped material. This damage may arise from at least three mechanisms: (1) single-photon absorption leading to local heating, (2) single-photon absorption leading to photochemical transformations, and (3) multiple-photon absorption leading to photochemical transformations. Events (1) and (2) may be mitigated by choosing a wavelength of light which is weakly absorbed by the trapping material and by the surrounding fluid medium. Event (3) is a more general problem and is mitigated in part by working with longer-wavelength light. Thus holographic optical traps may manipulate delicate materials more gently with greater effect by distributing smaller amounts of force continuously among a number of points on an object rather than potentially damaging the object by exerting the total force on a single point or at a higher intensity for a period of time.

In one embodiment consistent with the present invention, the design is flexible in that any desired pattern of channels 203 may be designed with a standard CAD/CAM computer program. The complexity of the pattern is not a factor as long as the channels 203 are far enough apart so as not to impinge on one another. As may be seen in FIGS. 2B and 3, multiple sets of channels 203 may be easily accommodated so that a single chip may be used for more than one experiment. In addition, once a mold is made it may be used to fabricate thousands of sample chambers so the methodology is readily adaptable to mass production techniques. It is estimated that the marginal cost of a single chamber would be of the order of a few cents when in mass production.

4. Optical System a. Synthesizing the Hologram

Early versions of the holographic optical traps used fixed holograms fabricated from a variety of materials. These were adequate to demonstrate the principle of using holograms to create up to several hundred traps. However the major shortcoming of these holograms was that they were static and it took hours to make a single hologram. With the advent of the hardware to create computer-driven liquid crystal displays capable of forming holograms many times per second, the use of optical traps as a dynamic device has become a practical reality. The principle for computing the hologram is described below.

b. The Microscope

The optical system 110 consists of a standard high quality light microscope. The objective is a high numerical aperture lens 109 coupled with a long working distance condenser lens. The high numerical aperture objective lens 109 is used for trapping. While the long working distance condenser lens may somewhat reduce the resolution in the images, it does not compromise trapping and provides extra space near the sample slide to accommodate plumbing and receptacles. The objects may be moved by holding them with traps and moving the stage of the microscope vertically or laterally.

In one embodiment consistent with the present invention, approximately 2 mW of laser power is employed to produce 200 microwatts at the trap. The power level available from a 2W laser is adequate to create about 1000 traps. A green laser (532 nm) is used, but other wavelengths may also be used, including, for example, a far red laser to work with materials absorbing near the 532 nm value.

Trapping depends upon the refractive index gradient so that materials with refractive indices close to that of the surrounding medium need traps with higher power levels. In addition, the tolerance of materials to damage will vary with trap power, so it is desirable for the user to be able to control this parameter. The user may increase the power level in any particular trap using a 'power slider' displayed on the graphical interface.

c. The Liquid Crystal Hologram (Also Referred to as a Spatial Light Modulator or SLM)

The spatial light modulator 108 is essentially a liquid crystal array controlled by an electrostatic field which, in turn may be controlled by a computer program. The liquid crystal array has the property that it retards the phase of light by differing amounts depending upon the strength of the applied electric field.

Nematic liquid crystal devices are used for displays or for applications where a large phase-only modulation depth is needed (2Π or greater). The nematic liquid crystal molecules usually lie parallel to the surface of the device giving the maximum retardance due to the birefringence of the liquid crystal. When an electric field is applied, the molecules tilt parallel to the electric field. As the voltage is increased the index of refraction along the extraordinary axis, and hence the birefringence, is effectively decreased causing a reduction in the retardance of the device.

d. The Laser

Useful lasers include solid state lasers, diode pumped lasers, gas lasers, dye lasers, alexandrite lasers, free electron lasers, VCSEL lasers, diode lasers, Ti-Sapphire lasers, doped YAG lasers, doped YLF lasers, diode pumped YAG lasers, and flash lamp-pumped YAG lasers. Diode-pumped Nd:YAG lasers operating between 10 mW and 5 W are preferred. The preferred wavelengths of the laser beam used to form arrays for investigating biological material include the infrared, near infrared, visible red, green, and visible blue wavelengths, with wavelengths from about 400 nm to about 1060 nm being most preferred.

5. Method of Operation

In one embodiment consistent with the present invention, an optical trapping system 500 (see FIG. 5) (such as the BioRyx system sold by Arryx, Inc., Chicago, Ill.) includes a Nixon TE 2000 series microscope 501 into which a mount for forming the optical traps using a holographic optical trapping unit 505 has been placed. The nosepiece 502 to which is attached a housing, fits directly into the microscope 501 via the mount. For imaging, an illumination source 503 is provided above the objective lens 504 to illuminate the sample 506.

In one embodiment of the present invention, the optical trap system 100 (see FIGS. 1 and 5) includes one end of the first light channel which is in close proximity to the optical element, and the other end of the first light channel which intersects with and communicates with a second light channel formed perpendicular thereto. The second light channel is formed within a base of a microscope lens mounting turret or "nosepiece". The nosepiece is adapted to fit into a Nixon TE 200 series microscope. The second light channel communicates with a third light channel which is also perpendicular to the second light channel. The third light channel traverses from the top surface of the nosepiece through the base of the nosepiece and is parallel to an objective lens focusing lens 109. The focusing lens 109 has a top and a bottom forming a back aperture. Interposed in the third light channel between the second light channel and the back aperture of the focusing lens is a dichroic mirror beam splitter 108.

Other components within the optical trap system for forming the optical traps include a first mirror, which reflects the beamlets emanating from the phase patterning optical element 101 through the first light channel, a first set of transfer optics 106 disposed within the first light channel, aligned to receive the beamlets reflected by the first mirror, a second set of transfer optics 107 disposed within the first light channel, aligned to receive the beamlets passing through the first set of transfer lenses, and a second mirror 108, positioned at the intersection of the first light channel and the second light channel, aligned to reflect beamlets passing through the second set of transfer optics and through the third light channel.

To generate the optical traps, a laser beam is directed from a laser 507 (see FIG. 5) through a collimator and through an optical fiber end 508 and reflected off the dynamic surface of the diffractive optical element 509. The beam of light exiting the collimator end of the optical fiber is diffracted by the dynamic surface of the diffractive optical element into a plurality of beamlets. The number, type and direction of each beamlet may be controlled and varied by altering the hologram encoded in the dynamic surface medium. The beamlets then reflect off the first mirror through the first set of transfer optics down the first light channel through the second set of transfer optics to the second mirror; and are directed at the dichroic mirror 509 up to the back aperture of the objective lens 504, are converged through the objective lens 504, thereby producing the optical gradient conditions necessary to form the optical traps. That portion of the light which is split through the dichroic mirror 509, for imaging, passes through the lower portion of the third light channel forming an optical data stream (see FIG. 1).

Spectroscopy of a sample of biological material may be accomplished with an imaging illumination source 503 suitable for either spectroscopy or polarized light back scattering, the former being useful for assessing chemical identity, and the later being suited for measuring dimensions of internal structures such as the nucleus size. Using such spectroscopic methods, in some embodiments, cells are interrogated. A computer 510 may be used to analyze the spectral data and to identify cells bearing either an X or Y chromosome, or a suspected cancerous, pre-cancerous and/or non-cancerous cell types. The computer program then may apply the information to direct optical traps to contain selected cell types. The contained cells then may be identified based on the reaction or binding of the contained cells with chemicals.

The present method and system lends itself to a semi-automated or automated process for tracking the movement and contents of each optical trap. The movement may be monitored, via video camera 511, spectrum, or an optical data stream and which provides a computer program controlling the selection of cells and generation of optical traps.

In other embodiments, the movement of cells is tracked based on predetermined movement of each optical trap caused by encoding the phase patterning optical element. Additionally, in some embodiments, a computer program is used to maintain a record of each cell contained in each optical trap.

The optical data stream may then be viewed, converted to a video signal, monitored, or analyzed by visual inspection of an operator, spectroscopically, and/or video monitoring. The optical data stream may also be processed by a photodetector to monitor intensity, or any suitable device to convert the optical data stream to a digital data stream adapted for use by a computer.

In an approach which does not employ an SLM, movement is accomplished by transferring the objects from a first set of optical traps to a second, third, and then fourth etc. To move the objects from the first position to a second position, a static phase patterning optical element is rotated around a spindle to align the laser beam with a second region which generates the second set of optical traps at a corresponding second set of predetermined positions. By constructing the second set of optical traps in the appropriate proximity to the first position, the probes may be passed from the first set of optical traps to the second set of optical traps. The sequence may continue passing the probes from the second set of predetermined positions to a third set of predetermined positions, from the third set of positions to a fourth set of predetermined positions, and from the fourth set of predetermined positions and so forth by the rotation of the phase patterning optical element to align the appropriate region corresponding to the desired position. The time interval between the termination of one set of optical traps and the generation of the next is of a duration to ensure that the probes are transferred to the next set of optical traps before they drift away.

In a staggered movement of the objects from a wide to narrow proximity the staggered movement of the cells occurs in a similar fashion. However, as the objects are passed from a first set of optical traps to a second set and moved to second and subsequent positions, the staggered arrangement of the traps allows the objects to be packed densely without placing a set of traps in too close a proximity to two objects at the same time which could cause the objects to be contained by the wrong optical trap Once an object or cell has interacted with a trap, spectral methods may be used to investigate the cell. The spectrum of those cells which had positive results (i.e., those cells which reacted with or bonded with a label) may be obtained by using imaging illumination such as that suitable for either inelastic spectroscopy or polarized light back scattering. A computer may analyze the spectral data to identify the desired targets and direct the phase patterning optical element to segregate those desired targets. Upon completion of the assay, selection may be made, via computer and/or operator, of which cells to discard and which to collect.

Figure 9:
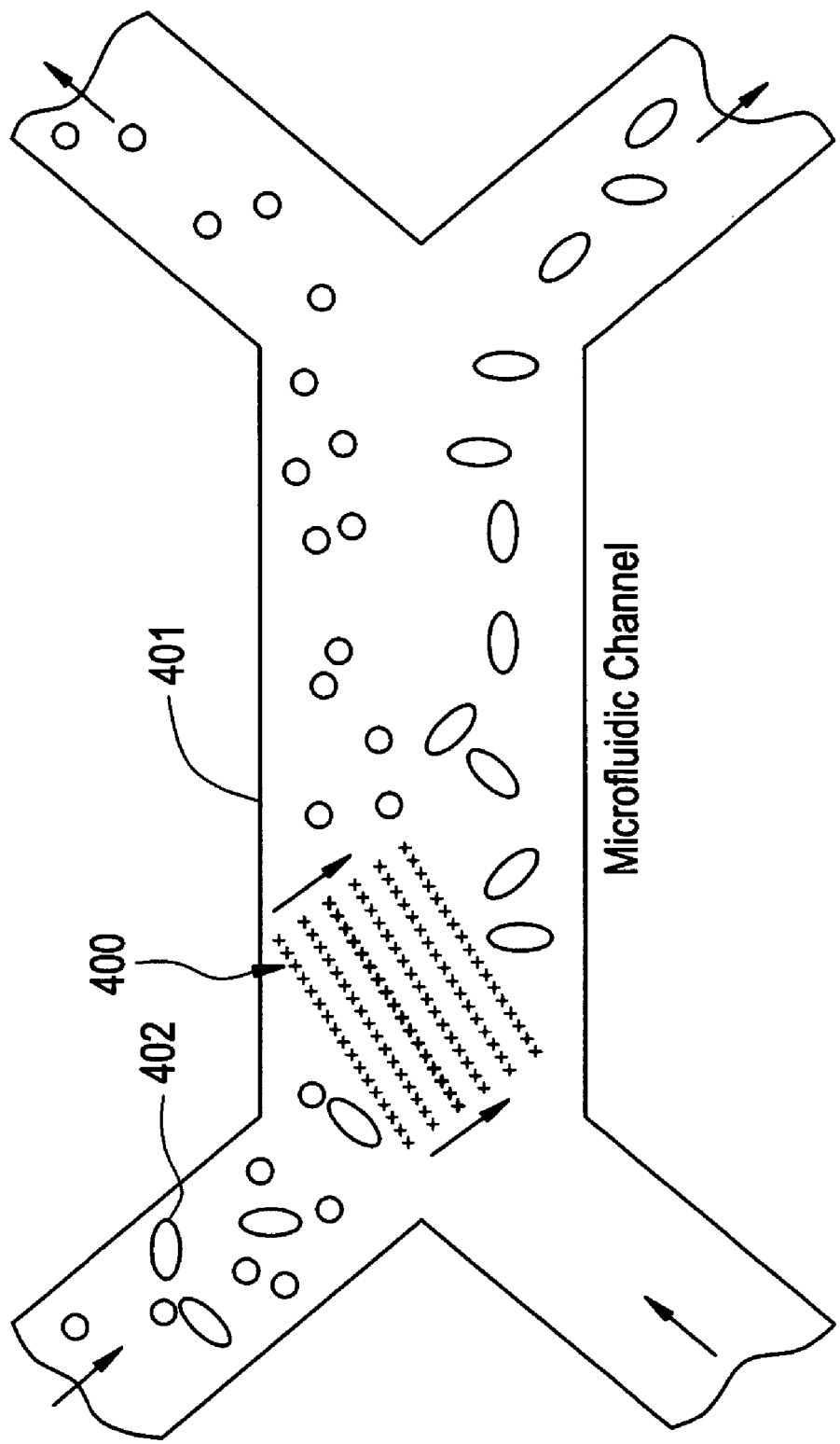
FIG. 9 illustrates optical peristalsis according to one embodiment consistent with the present invention.

Optical peristalsis (see FIG. 9) is an existing process employing parallel lines of traps 400 in a microfluidic channel 401 arranged so that the spacing between the lines permits particles 402 trapped in one line to be pulled into traps in the other line when the first line of traps is turned off. Optical peristalsis may be used as an alternative to and in conjunction with fluorescent labels (as described later regarding Applications). The process operates by timing the extinction of lines of traps timed so that particles are moved in desired directions specified by the arrangement of the lines of traps. By choosing whether a line of traps on one side or the other of a particle are on or off, the particle may be moved forward or back in a direction. By employing large numbers of traps, large numbers of particles may thus be moved in concert in a given direction. Thus, particles attracted to the traps may be moved to a given area and, if desired, collected there.

Similarly, by gradually reducing the spacing between traps in lines toward a given direction and/or varying the curvature of the lines of traps, particles may be swept into a focusing pattern to concentrate them. Reversing such a pattern would disperse the particles.

Spacing between lines of traps may be relatively larger to speed up movement of the particles, or relatively narrower to slow them down. Similarly, varying the intensity of selected traps or lines, and hence their effect on particles, may also be employed. By converging or diverging flows, particles may be combined or separated. In addition, optical peristalsis may be combined with differential effects of viscous drag or electrical fields to produce complex and specific sets of parameter values for finely separating materials, for example. By opposing the trapping and other forces, the balance point of the two forces determines whether a particle moves with the trap or the other force.

In one embodiment consistent with the present invention, optical peristalsis may be implemented with a holographic system which cycles through a sequence of phase patterns to implement a corresponding sequence of holographic optical trapping patterns. Such patterns may be encoded in the surface relief of reflective diffractive optical elements mounted on the face of a prism, wherein each pattern is rotated into place by a motor. Likewise, transmissive diffractive optical elements may be placed on the perimeter of a disk and rotated to cycle through the patterns. Switchable phase gratings and phase holograms encoded on film may also be used.

For particles driven past a rectilinear array by an external bias force, such as fluid flow, where the trapping force is considerably greater than the external driving force, the particles are trapped. Where the bias force is greater, the particles flow past the array. Between these extremes, the bias force exceeds the trapping force to a differing degree for different fractions of the particles, causing the particles to hop from trap to trap along the direction of the principal axis of the array. A zero net deflection may be observed where the array is rotated to 45° because: (1) positive and negative displacements occur with equal probability; or (2) the particles become locked into the [11] direction, jumping diagonally through the array.

Particles affected to a greater degree by an array may be deflected to greater angles than the particles affected to a greater degree by the bias force. The optical gradient force exerted on particles varies roughly as $a^3$, where a=radius. Stokes drag on the particles varies as "a". Thus, larger particles are disproportionately affected by trap arrays, while the smaller particles experience smaller deflection. Orienting the array near the angle of optimal deflection and adjusting the intensity to place the largest particles in the hopping condition, and, hence at greater deflection than smaller particles. Differentially deflected particles may be collected or further fractionated by additional arrays downstream of the first.

Some conventional techniques for fractionation achieve separation in the direction of an applied force. However, such techniques operate on batches of samples rather than continuously.

Other conventional techniques for microfractionation employ microfabricated sieves consisting of a two dimensional lattice of obstacles or barriers. For example, an asymmetric placement of barriers rectifies the Brownian motion of particles that pass through the sieve, causing the particles to follow paths that depend on the diffusion coefficients of the particles. However, use of a microfabricated lattices clog and are not tunable for particle size and type.

Figure 6:
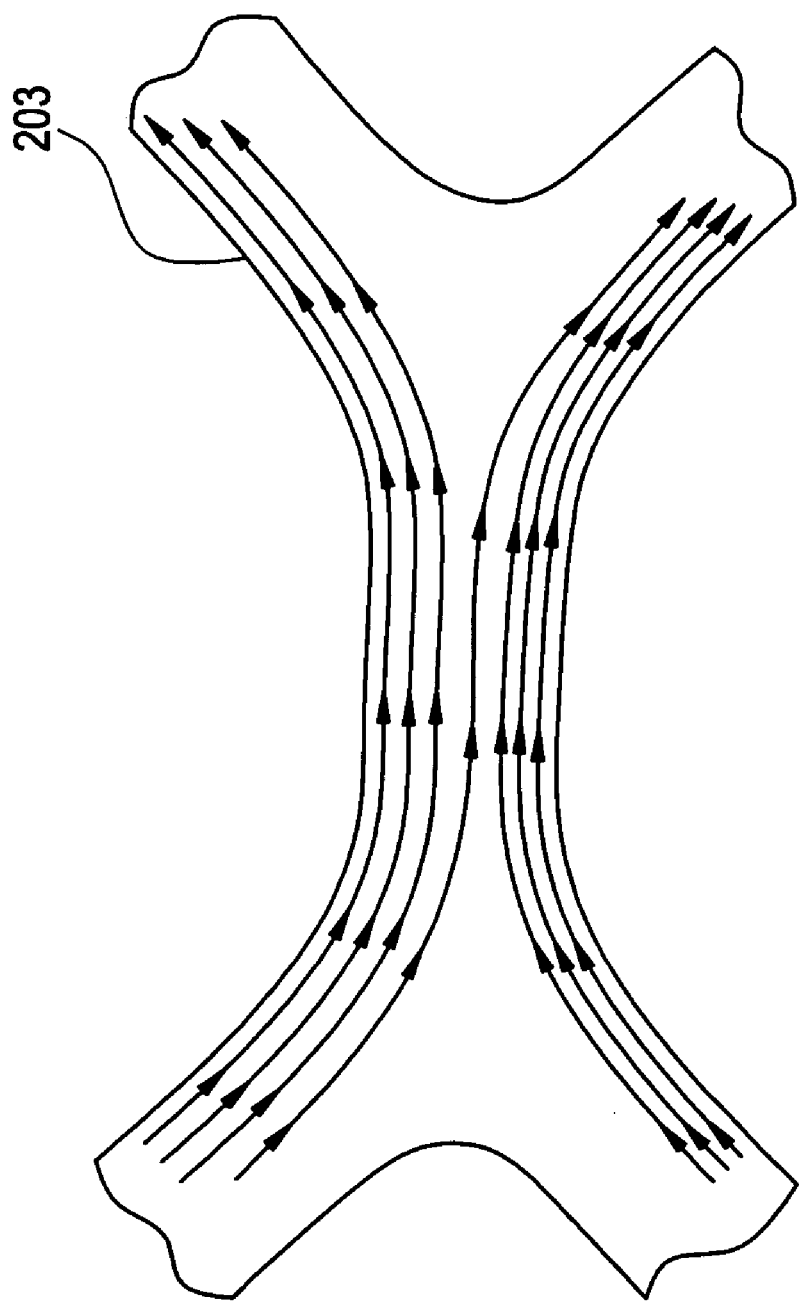
FIG. 6 illustrates an example of lateral deflection for sorting according to one embodiment consistent with the present invention.

In FIG. 6, an example of sorting of particles according to the present invention is exemplified. Although the illustrated example exemplifies lateral deflection, optical peristalsis may be obtained in the same system. A representation of a video image shows light-based separation of material, in this case, tuned to separate objects based on particle size. The flow in the upper left channel contains 1, 2.25, and 4.5 µm particles and another flow enters from the lower left. The superimposed lines respectively indicate each of the channels' flow when the system laser power is off. When the laser power is turned on, light in the interaction region (indicated by the superimposed green box), extracts the 4.5 µm particles from the upper flow and delivers them to the lower-right channel as indicated by the superimposed white path.

6. Application in Sperm Sorting a. Background

In one application consistent with the present invention, a high-resolution, high-throughput cell sorter by using optical trapping technology is implemented. The need for implementing this technology as a new basis for cell sorting is evidenced by the failure of traditional flow cytometers to perform the high-resolution determinations of cell characteristics necessary in many sorting problems. In this example of separating X- and Y-chromosome bearing sperm from one another in the cattle industry, flow rates are scaled back substantially from state-of-the-art systems rates of today. The reason is that traditional flow cytometry is best at making a fluorescence/non-fluorescence determination and, in this mode, may operate at rates yielding outputs of 30,000 cells/second. As the problem becomes one of discriminating between different levels of fluorescence (as it is in the sperm separation problem), these methods become highly inefficient. In the sperm separation problem, where the X- and Y-chromosome bearing sperm differ in fluorescence by about 4%, the rate is slowed to about 4,000 output cells per second. (see J. L. Schenk, et al., Proceedings, The Range Beef Cow Symposium XVI, 1999.)

b. Sorting Using Holographic Optical Traps

The method of implementing high-resolution, high-throughput cell sorting of the present invention, has the following components: microfluidic development, optical-trap system development (trapping component for the funnel system and the trap component for the separation system), high-resolution fluorescence measurement, system control (including hologram calculation), and mechanical design.

The first component is a flow cell that has a fluid input channel, carrying the input sample, and two output channels carrying cells separated out of the input channel. The second component is a set of traps that perform the "funneling" function (this "funneling function" is the equivalent of the nozzle forming the droplet flow in a traditional flow cytometer). The third component is the detection system and, finally, the fourth component is the sorting system. FIGS. 7A–7B illustrate the relationship among these four components.

In this example, sperm is used as a sample target for separation. The traditional method of differentiating between X- and Y-chromosome bearing sperm employs Hoechst 33342, a dye which binds specifically to DNA in such a way that the total fluorescence present is a measure of the total DNA present. Measurements of this fluorescence yields an estimate of the nature of the underlying chromosome load. (Schenk, 1999; also, Erik B. van Munster, Cytometry, volume 47, page 192, 2002).

The essential trait allowing this proposed embodiment of the present invention to achieve high throughputs is its inherent capacity to run material in parallel lines simultaneously and in close proximity to one another. For this initial implementation, a flow system with 10 input lines 300 each separated by 10 microns is created. This sets an overall width to the flow from the input reservoir of 110 microns. The output channels 302, 303 are each the same 110 micron width as the input channel 301 and they run parallel to the input channel 301 as is shown in FIGS. 7A and 7B. Introduced into the "output channels" 302, 303 is a buffer solution that is fed into these channels at the same flow rate as is maintained in the input channel 301. All three of these channels 301, 302, 303 are designed to maintain laminar flow over the flow ranges of interest. In the sorting region, where specific cells are transferred from the input channel 301 to one of the output channels 302, 303, all three flows are adjacent with no mechanical separation between them. The laminar flows keep any material in their respective flows unless a specific external force is introduced to transfer that material from one flow channel to another.

The funneling traps 305 act on the input cells 306 so they both travel in well defined lines of flow and so the input cells 306 are separated from one another by a minimum distance 306 to be set by the operator. The flow rates in the channels 301, 302, 303 are set by this minimum distance 306, by the "update" rate of the device that is performing the separation function, and by the overall cell processing rate desired. Assuming that minimum distance in our sample case is 20 microns (enough to completely separate the sperm heads, but a distance that will allow an inconsequential overlapping of tails), and a processing rate of 1,500 cells/second, this system uses a flow rate of 3 mm/second [(15,000 cells/second)×(20 microns/cell-line)÷(10 lines)]. (check this)

The funneling system is composed of a pattern of low intensity traps 305 established by a set of static holograms that are mounted in a rotating wheel so that the pattern changes as a function of the rotation pattern. The most down stream funneling traps are of fixed intensity and position, serving only to maintain the separation between the cells' lines of flow. The upstream traps 305 are allowed to change both intensity and position with time to act so as to disturb the flow on clumped cells and pass through individual, or un-clumped, cells.

The measurement upon which the sorting determination is made may occur in the downstream region of the funneling traps 305 or it may occur in a region further beyond the funneling system. For this initial system, the measurement will consist of high resolution fluorescence detection. In the future, however, other active sorting criteria may be implemented, such as scattering measurements, or passive techniques may be employed such as those using optical deflection as outlined earlier.

The final component of the device is the separation system in which the sorting criteria is utilized to divert cells into one of the output channels 302, 303 or to allow them to remain in the flow of the input channel 301. The crucial parameter for this component is the field-of-view of the high-numerical-aperture objective lens 304 used to implement the array of dynamic traps 305 driving the separation. The width of this field-of-view is the same 110 microns as the individual channels' widths. The length, however, depends upon the flow rates, the channel depths, and the update rates of the optical device used to control these traps.

Currently, one embodiment consistent with the present invention includes spatial light modulators that create phase masks which are highly effective in driving optical trapping systems. These devices have update rates of 30 Hz or more. With an estimated channel depth of 10 microns, and assuming that the sperm cells should be moved in 1 micron steps, 10 updates of the spatial light modulator are employed to move a cell from the center of the input channel 301 to the center of either output channel 302, 303. With an update value of 30 Hz, the implementation of these 10 steps will occur in ⅓ second. At a flow rate of 3 mm/second, these 10 steps are implemented on a length of 1 mm in the direction of flow. The objective lens 304 for the separation component would therefore have a working area of 110 microns×1000 microns. An important development area of this project is the design of this lens assembly. The trade-off in lens design generally is between field-of-view and numerical aperture. That is, for a lens assembly of a particular complexity, a significant performance increase in one of these areas will come with a decrease in performance in the other area. It is for this reason that the high-performance lenses used in areas such as the high-resolution lithographic production of integrated-circuit electronics are quite complex. The present invention; however, is significantly below the performance levels of these lens assemblies.

7. Disclosure on Wide-Field Vortex Tweezing

Tweezing with a wide field of view involves microscope objective lenses that have a relatively low numerical aperture. The ability to optically trap objects in the axial direction relies on focusing a light beam down in a manner that will have the largest gradients in the axial direction. This implies that a cone of light be formed with the broadest possible radius. The radius of the cone is directly determined by the numerical aperture of the objective, i.e., high numerical aperture means a broad cone radius. This is in direct conflict with the requirements for wide field of view. This has traditionally made tweezing with a wide field of view in the axial direction difficult. One of the major contributions to the difficulty in axial tweezing is the radiation pressure of the focused light beam. Especially for particles that are well matched in density to the surrounding medium, for example polystyrene microspheres, radiation pressure may blow particles out of the trap. With a low numerical aperture objective, it is difficult to overcome the radiation pressure with sufficient tweezing force in the axial direction. However, holographic optical traps have the ability to form exotic modes of light which greatly reduce the radiation pressure of the light beam. Vortex traps, for example, have a dark center because the varying phases of light cancel in the center of the trap. This dark center means most of the rays of light which travel down the center of the beam no longer exist. It is exactly these beams which harbor most of the radiation pressure of the light, so their removal greatly mitigates the difficulty in axial trapping. Other modes, e.g. donut modes, have the same advantage.

Manipulation (pushing, steering, sorting) of objects or cells in general, is made safer by having multiple beams available. Like a bed of nails, multiple tweezers ensure that less power is introduced at any particular spot in the cell. This eliminates hot spots and reduces the risk of damage. Any destructive two-photon processes benefit greatly since the absorption is proportional to the square of the laser power. Just adding a second tweezer decreases two-photon absorption in a particular spot by a factor of four. Large cells like *Tetrahymena*, which are held in place by an array of tweezers, involve a large amount of laser power for effective trapping. Putting the power into a single trap would cause immediate damage to the cell.

Finally, manipulation of even just a single cell is greatly enhanced by utilizing holographic optical trapping. A single epithelial cheek cell can be manipulated by a line of tweezers, which lift the cell along the perimeter on one side. The resulting rotation allows a 360 degree view of the cell. In addition to the advantage for viewing of biological samples, there also exists the ability to orient samples stably, which has clear benefit for studies such as scattering experiments which have a strong dependence on orientation of the sample.

8. Spinning Disk-Based Cell Sorter

Because of the large number of sperm in a typical bovine ejaculate, and the small amount of time available before the sperm becomes no longer functional, a large number of sperm per second (on the order of a million) are sorted for a commercially viable sperm sorter. Sorting with holographic optical traps confers enormous advantage through its ability to process in parallel a large number of cells.

The technology for using lasers to access a large number of sites quickly already exists in the form of a spinning laser disc, CD player, or DVD player. These devices combine rotational motion of the disc with radial motion of the laser to access sites with incredibly high speeds. For example, the typical DVD player may access approximately 4 billion separate "bits" on the disc in about two hours. Combining this spinning disc approach with optical trapping (see FIG. 8) allows access to cells at similar rates, and holographic optical trapping increases these rates by factors of 100 or even higher.

Figure 8:
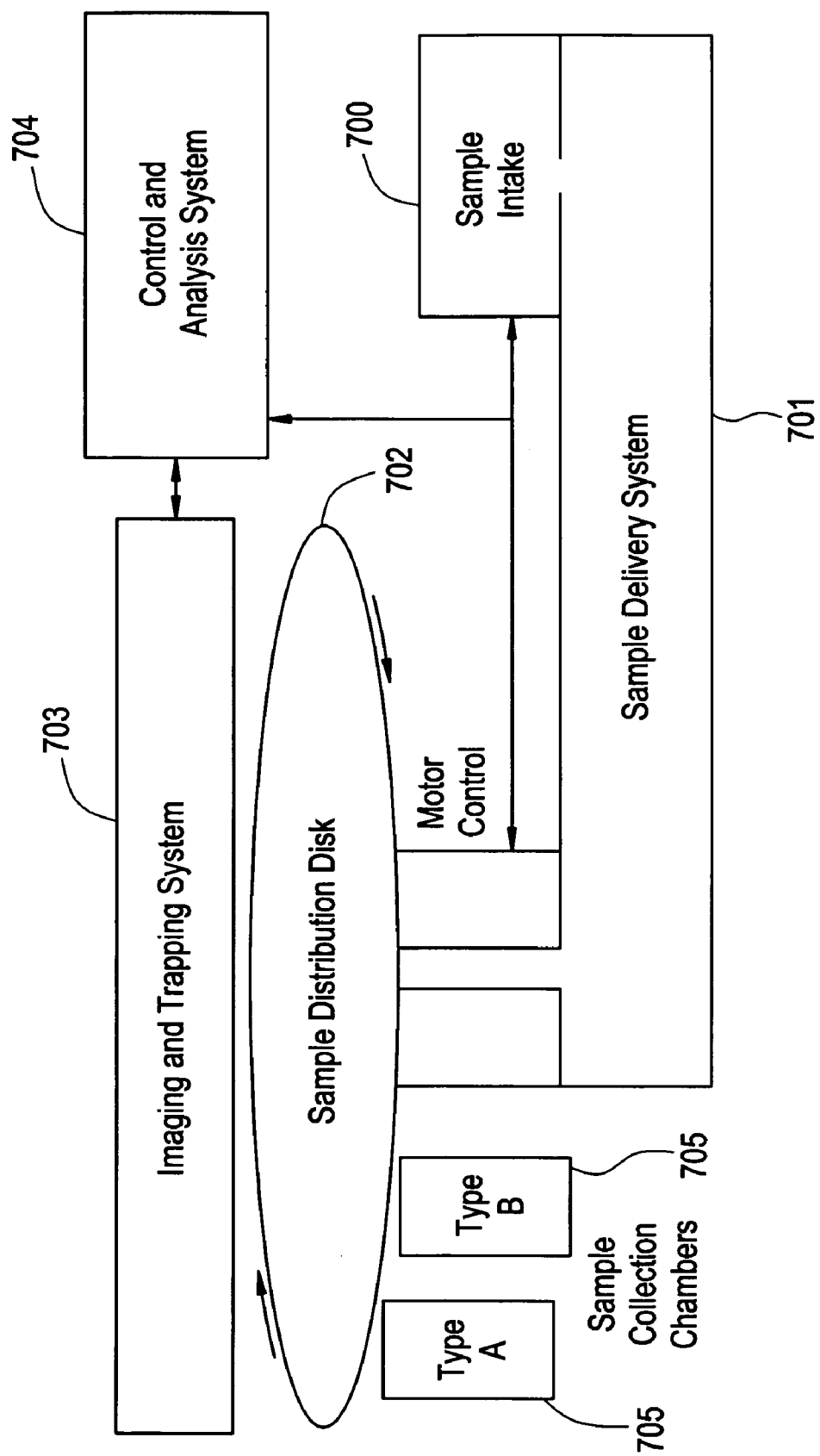
FIG. 8 illustrates a spinning disc-based cell sorted according to one embodiment consistent with the present invention.

As shown in FIG. 8, objects or cells are introduced at the sample intake 700, and using an appropriate sample delivery system 701, the cells are provided to the sample distribution disc 702 which is rotated by a motor control. The imaging and trapping system 703, which is connected to a control and analysis system 704, sorts the cells and they are collected in sample chambers 705 and 706.

There are many mechanisms for distributing the cells over the surface of the disc. Fluid chambers which house individual cells, gels which immobilize the cells, sticky or waxy surfaces which bind the cells, or even freezing the cells into a solid mass, are all methods that may be employed. Once the cells are situated such that they maintain their relative positions, they may be appropriately measured. Optical trapping may then be used to free either the desired or unwanted cells from the surface or volume. In situations where sorting into more than two groups is desired, each group may be released in a single pass, and multiple passes may be executed.

9. Sorting of Cells and Non-Biological Material Using Meltable Substrates

Technologies such as Fluorescence-Activated Cell Sorting (FACS), although well-established, suffer from the fact that they are serial processing methods. Because of the ubiquity of labeling dyes in biology, sorting on the basis of these dyes is possible. These dyes often create a difference in absorption of some wavelength or range of wavelengths between dyed and undyed specimens, assuming that groups that are to be sorted do not already inherently exhibit such an absorption difference. Holographic optical traps may then be used to both heat and manipulate the specimen into a substrate which melts from the raised temperature of the specimen. The specimen which is embedded may then be released later with an increase in the bulk temperature. In addition, a faster, even more parallel processing method is possible in which the cells are illuminated by a broad, high power light source which processes the entire array of specimens simultaneously. The same set of methods may be applied to non-biological samples which differ in the absorption spectra, or may be selectively made to do so.

10. Gel-based Sorting

Holographic optical laser traps construe a great advantage on the manipulation of objects in that they are able access and move objects in three dimensions. As biological sorting applications become more advanced, larger numbers of specimens need to be sorted, often in small amounts of time. The three-dimensional access of holographic optical traps means that these sorting applications may be realized. Quantities of cells and other specimens of biological interest which would be cumbersome or impossible to sort serially or on a two-dimensional substrate, may be effectively sorted.

One implementation of such three dimensional sorting relies on a reversible gelation process. The cells are gelled in a network, and then either wanted or unwanted cells are extracted from the gel using holographic optical traps. The heat from the traps may be used to melt the gel and provide exit pathways.

Alternatively, cells are selectively killed based on some criterion with the holographic optical laser traps. The entire gel is then melted and the live cells are separated from the dead. Instead of just killing, a more destructive thermal explosion may be generated, which disintegrates the cell into much smaller components, and then sorting on the basis of size may be effected, grouping or connecting certain cells together again.

11. Killing of Biological Specimens

A large variety of applications benefit from the ability to selectively kill biological specimens. Removing pathogens from blood is one such application. Cell sorting is another application. Cells are identified, one or more groups of cells are killed, and then the dead cells are removed. The killing is performed by the light energy from the lasers themselves, and do not necessarily require optical traps to perform this function.

Essentially, the cells are heated or the medium around the cells are heated with the laser beam, damaging and killing the cell. Holographic optical traps, because of their versatility and three-dimensional control, allow selective, massively parallel killing of cells.

12. Fixing Electronic Components

Note that many of the above techniques can be used to move small electronic components or to fix electronic components in place.

While the invention has been particularly shown with reference to the above embodiments, it will be understood by those skilled in the art that various other changes in the form and details may be made therein without departing from the spirit and the scope of the invention.

What is claimed is:

1. A method of sorting objects comprising: distributing the objects over a surface of a structure; and evaluating the objects in said structure according to a predetermined criteria using a beam steering apparatus;
wherein said structure is a disc.

2. The method according to claim 1, further comprising: combining rotational motion of said disc with radial motion of a laser to access the objects.

3. The method according to claim 2, further comprising: ensuring the objects maintain their relative positions on said disc.

4. The method according to claim 3, wherein said ensuring step comprises: providing each of the objects in a fluid chamber.

5. The method according to claim 3, wherein said ensuring step comprises: providing an adhering surface to bind the objects.

6. The method according to claim 3, further comprising: measuring the objects to ascertain their relative positions.

7. A method of sorting objects comprising:
distributing the objects over a surface of a structure: and evaluating the objects in said structure according to a predetermined criteria using a beam steering apparatus; wherein said structure is a meltable substrate, and said substrate is heated to melt a surface of said substrate, and the objects are embedded in said surface of said substrate.

8. The method according to claim 7, wherein the objects are released from said surface of said substrate when said substrate is reheated.

9. The method according to claim 7, wherein said predetermined criteria is a predetermined absorption spectra.

10. The method according to claim 3, wherein the objects which do not meet said criteria are killed.

11. An apparatus for sorting objects comprising: a beam steering apparatus; and a structure having a surface on which the objects are distributed; wherein the objects are sorted using said bean steering apparatus, according to whether the objects meet predetermined criteria; wherein said structure is a disc.

12. The apparatus according to claim 11, wherein a rotational motion of said disc is combined with a radial motion of a laser from said beam steering apparatus, to access the objects.

13. The apparatus according to claim 11, wherein the objects maintain their relative positions on said disc.

14. An apparatus for sorting objects comprising: a beam steering apparatus; and a structure having a surface on which the objects are distributed; wherein the objects are sorted using said bean steering apparatus, according to whether the objects meet predetermined criteria; wherein said structure is a substrate, and said substrate is heated to melt a surface of said substrate, and the objects are embedded in said surface of said substrate.

15. The apparatus according to claim 14, wherein the objects are released from said surface of said substrate when said substrate is reheated.

16. The apparatus according to claims 11 or 14, wherein said predetermined criteria is a predetermined absorption spectra.

17. An apparatus for sorting objects comprising: means for distributing the objects over a surface of a structure; and means for evaluating the objects in said structure according to predetermined criteria using a beam steering apparatus;
wherein said structure is a meltable substrate, and the substrate is heated to melt a surface of the substrate, and the objects are embedded in the surface of the substrate.

18. An apparatus for sorting objects comprising: a beam steering apparatus including: a laser which provides a laser beam for illumination; a diffractive optical element which diffracts said beam into a plurality of beamlets; and an objective lens which converges the beamlet, thereby producing optical gradient conditions resulting in an optical data stream to form an optical trap; and a sample chamber into which the objects are introduced, trapped and sorted; wherein said optical element has one of a static and a dynamic surface.

19. The apparatus according to claim 18, wherein the objects are moved by holding them with said optical trap and moving a stage of the microscope vertically or laterally.

20. The apparatus according to claim 18, wherein said optical element is a liquid crystal array controlled by an electrostatic field.

21. The apparatus according to claim 20, wherein said liquid crystal of said liquid crystal array is a nematic liquid crystal.

22. The apparatus according to claim 18, wherein said optical element includes at least one fixed surface region.

23. An apparatus for sorting objects comprising: a beam steering apparatus including: a laser which provides a laser beam for illumination; a diffractive optical element which diffracts said beam into a plurality of beamlets; and an objective lens which converges the beamlet, thereby producing optical gradient conditions resulting in an optical data stream to form an optical trap; and a sample chamber into which the objects are introduced, trapped and sorted; wherein said optical element includes gratings, holograms, lenses, mirrors, prisms, and waveplates.

24. An apparatus for sorting objects comprising: a beam steering apparatus including: a laser which provides a laser beam for illumination; a diffractive optical element which diffracts said beam into a plurality of beamlets; and an objective lens which converges the beamlet, thereby producing optical gradient conditions resulting in an optical data stream to form an optical trap; and a sample chamber into which the objects are introduced, trapped and sorted; wherein said optical element has a time dependent function.

25. An apparatus for sorting objects comprising: a beam steering apparatus including: a laser which provides a laser beam for illumination; a diffractive optical element which diffracts said beam into a plurality of beamlets; and an objective lens which converges the beamlet, thereby producing optical gradient conditions resulting in an optical data stream to form an optical trap; and a sample chamber into which the objects are introduced, trapped and sorted; wherein said objective lens has a relatively low numerical aperture.

26. The apparatus according to claim 18, further comprising an imaging system.

27. The apparatus according to claim 26, wherein said imaging system is a camera.

28. The apparatus according to claim 26, further comprising: a display.

29. The apparatus according to claim 18, wherein a power level of said optical trap is monitored.

30. The apparatus according to claim 18, wherein said optical trap is a holographic optical trap.

31. The apparatus according to claim 30, wherein a height of said optical trap can be changed.

32. The apparatus according to claim 31, wherein said height change is performed by adjusting said hologram such that said light beam forming said optical trap one of converges and diverges as it enters said objective lens.

33. The apparatus according to claim 32, wherein an adjustment of phase modulation caused by said hologram adjusts said height of said one optical trap to change independently of another optical trap.

34. The apparatus according to claim 18, wherein said sample chamber comprises: a plurality of channels for introducing the objects.

35. The apparatus according to claim 34, wherein said channels are connected to tubing by syringe needles, the tubing which lead to supply and collection reservoirs.

36. The apparatus according to claim 35, wherein the objects are suspended in a liquid medium.

37. The apparatus according to claim 35, wherein micropumps introduce said liquid medium with suspended objects into said channels of said sample chamber.

38. The apparatus according to claim 34, wherein said channels are 50 microns wide and 50 microns deep.

39. The apparatus according to claim 18, wherein said sample chamber is made of a PDMS resin.

40. The apparatus according to claim 30, wherein said holographic optical trap manipulates said object by distributing relatively smaller amounts of force continuously among a number of points on said object.

41. The apparatus according to claim 18, wherein said object is identified according to predetermined criteria prior to sorting.

42. The apparatus according to claim 41, wherein said object is identified using spectroscopy.

43. The apparatus according to claim 42, wherein said spectroscopy is performed by illuminating said object using an imaging illumination source.

44. The apparatus according to claim 43, wherein a chemical identity of the object is assessed.

45. The apparatus according to claim 43, wherein a measurement of an internal structure of the object is performed.

46. The apparatus according to claim 41, wherein said object which meets said predetermined criteria is contained by said optical trap.

47. The apparatus according to claim 46, wherein said object is identified based on one of a reaction and binding of said contained object with predetermined chemicals.

48. The apparatus according to claim 18, wherein at least one of a movement and contents of each optical trap is monitored.

49. The apparatus according to claim 48, wherein said movement of said object is tracked based on a predetermined movement of each optical trap caused by encoding said optical element.

50. The apparatus according to claim 48, wherein a record of each object contained in each optical trap is maintained.

51. The apparatus according to claim 18, wherein said optical data stream is processed to monitor its intensity.

52. An apparatus for sorting objects comprising: a beam steering apparatus including: a laser which provides a laser beam for illumination; a diffractive optical element which diffracts said beam into a plurality of beamlets; and an objective lens which converges the beamlet, thereby producing optical gradient conditions resulting in an optical data stream to form an optical trap; and a sample chamber into which the objects are introduced, trapped and sorted; wherein said object is transferred from one optical trap to a second optical trap.

53. The apparatus according to claim 52, wherein said object is transferred by using a static phase patterning optical element rotated around a spindle to align said laser beam with another region which generates a second set of optical traps at a corresponding set of predetermined positions proximate to said one optical trap.

54. The apparatus according to claim 52, wherein an arrangement of said optical traps is staggered.

55. The apparatus according to claim 42, wherein when said object meets said criteria, said object is labeled.

56. The apparatus according to claim 52, wherein said object is transferred by optical peristalsis.

57. The apparatus according to claim 56, wherein a focusing pattern of the objects is formed by at least one of reducing a spacing between said optical traps in lines toward a predetermined direction and reducing a curvature of said lines of said optical traps.

58. The apparatus according to claim 57, wherein a focusing pattern of the objects is dispersed by at least one of increasing a spacing between said optical traps in lines toward a predetermined direction and increasing a curvature of said lines of said optical traps.

59. The apparatus according to claim 57, wherein movement of the objects is increased by increasing said spacing between said lines of said optical traps.

60. The apparatus according to claim 58, wherein movement of the objects is decreased by decreasing said spacing between said lines of said optical traps.

61. An apparatus for sorting objects comprising: a beam steering apparatus including: a laser which provides a laser beam for illumination; a diffractive optical element which diffracts said beam into a plurality of beamlets; and an objective lens which converges the beamlet, thereby producing optical gradient conditions resulting in an optical data stream to form an optical trap; and a sample chamber into which the objects are introduced, trapped and sorted; wherein an intensity of selected optical traps and lines of said optical traps is varied.

62. The apparatus according to claim 56, wherein said optical peristalsis is combined with differential effects of one of viscous drag and electric fields.

63. The apparatus according to claim 62, wherein said optical peristalsis is implemented with a holographic system which cycles through a sequence of phase patterns to implement a corresponding sequence of holographic optical trapping patterns.

64. The apparatus according to claim 63, wherein said patterns are encoded on a surface of said optical element which is rotated to cycle through each pattern.

65. The apparatus according to claim 64, wherein switchable phase gratings and phase holograms encoded on film are used.

66. An apparatus for sorting objects comprising: a beam steering apparatus including: a laser which provides a laser beam for illumination; a diffractive optical element which diffracts said beam into a plurality of beamlets; and an objective lens which converges the beamlet, thereby producing optical gradient conditions resulting in an optical data stream to form an optical trap; and a sample chamber into which the objects are introduced, trapped and sorted; wherein a bias force is increased such that objects flow past a rectilinear array rather than being trapped by said optical traps.

67. The apparatus according to claim 66, wherein said bias force can differ causing said object to move from optical trap to optical trap along a direction of a principal axis of said array.

68. The apparatus according to claim 18, wherein the objects are sperm, and X-chromosome bearing sperm are sorted from Y-chromosome bearing sperm.

69. The apparatus according to claim 41, wherein when the objects are sorted into objects that meet said predetermined criteria and objects that do not meet said predetermined criteria, the objects that do not meet said predetermined criteria are killed.

70. The apparatus according to claim 11, wherein the beam steering apparatus is an optical trapping apparatus.

71. An apparatus for sorting objects comprising: a beam steering apparatus including: a laser which provides a laser beam for illumination; a diffractive optical element which diffracts said beam into a plurality of beamlets; an objective lens which converges the beamlet, thereby producing optical gradient conditions resulting in an optical data stream to form an optical trap; a sample chamber into which the objects are introduced, trapped and sorted; and a beam splitter which controls each beamlet by altering a hologram encoded in a dynamic surface medium of the diffractive optical element.

* * * * *